US010679385B1

(12) United States Patent
Yanoff et al.

(10) Patent No.: US 10,679,385 B1
(45) Date of Patent: Jun. 9, 2020

(54) SYSTEM AND METHOD FOR STATISTICAL ITERATIVE RECONSTRUCTION AND MATERIAL DECOMPOSITION

(71) Applicant: General Electric Company, Schenectady, NY (US)

(72) Inventors: Brian David Yanoff, Niskayuna, NY (US); Mingye Wu, Glenville, NY (US); Lin Fu, Niskayuna, NY (US); Peter Michael Edic, Albany, NY (US); Xue Rui, Jersey City, NJ (US); Geng Fu, Rexford, NY (US); Yannan Jin, Niskayuna, NY (US); Fredrik Gronberg, Stockholm (SE)

(73) Assignee: GENERAL ELECTRIC COMPANY, Niskayuna, NY (US)

( * ) Notice: Subject to any disclaimer, the term of this patent is extended or adjusted under 35 U.S.C. 154(b) by 0 days.

(21) Appl. No.: 16/221,606

(22) Filed: Dec. 17, 2018

(51) Int. Cl.
*A61B 6/00* (2006.01)
*G06T 11/00* (2006.01)
(Continued)

(52) U.S. Cl.
CPC ............ *G06T 11/005* (2013.01); *A61B 6/032* (2013.01); *A61B 6/4233* (2013.01);
(Continued)

(58) Field of Classification Search
CPC ....... G06T 11/005; G01T 1/171; G01T 1/366; G01T 1/249; G01T 1/1663;
(Continued)

(56) References Cited

U.S. PATENT DOCUMENTS

| 9,123,098 B2 | 9/2015 | Takahashi et al. |
| 9,261,467 B2 | 2/2016 | Thibault et al. |

(Continued)

OTHER PUBLICATIONS

Bornefalk et al., "Allowable forward model misspecification for accurate basis decomposition in a silicon detector based spectral CT," 2015, IEEE Transaction on medical imaging, vol. 34, No. 3, pp. 788-795. (Year: 2015).*

(Continued)

*Primary Examiner* — Kiho Kim
(74) *Attorney, Agent, or Firm* — Fletcher Yoder, P.C.

(57) ABSTRACT

A method for imaging an object to be reconstructed includes acquiring projection data corresponding to the object. Furthermore, the method includes generating a measured sinogram based on the acquired projection data and formulating a forward model, where the forward model is representative of a characteristic of the imaging system. In addition, the method includes generating an estimated sinogram based on an estimated image of the object and the forward model and formulating a statistical model based on at least one of pile-up characteristics and dead time characteristics of a detector of the imaging system. Moreover, the method includes determining an update corresponding to the estimated image based on the statistical model, the measured sinogram, and the estimated sinogram and updating the estimated image based on the determined update to generate an updated image of the object. Additionally, the method includes outputting a final image of the object.

21 Claims, 13 Drawing Sheets

(51) Int. Cl.
*G01T 1/166* (2006.01)
*G01T 1/36* (2006.01)
*G01T 1/17* (2006.01)
*A61B 6/03* (2006.01)
*G01T 1/24* (2006.01)
*G01N 23/046* (2018.01)

(52) U.S. Cl.
CPC .......... *A61B 6/4241* (2013.01); *A61B 6/4266* (2013.01); *A61B 6/5258* (2013.01); *G01N 23/046* (2013.01); *G01T 1/1663* (2013.01); *G01T 1/171* (2013.01); *G01T 1/249* (2013.01); *G01T 1/366* (2013.01); *G06T 11/003* (2013.01); *G01N 2223/401* (2013.01); *G01N 2223/419* (2013.01)

(58) Field of Classification Search
CPC ........ G01N 2223/401; G01N 2223/419; A61B 6/4233; A61B 6/032; A61B 6/4241; A61B 6/4266
See application file for complete search history.

(56) References Cited

U.S. PATENT DOCUMENTS

| | | | |
|---|---|---|---|
| 9,292,946 | B2 | 3/2016 | Zou |
| 9,501,819 | B2* | 11/2016 | Ra ..................... G06T 11/005 |
| 10,489,940 | B2* | 11/2019 | Case ................... G06T 11/005 |
| 2009/0039273 | A1 | 2/2009 | Tkaczyk et al. |
| 2010/0215230 | A1 | 8/2010 | Bornefalk et al. |
| 2014/0328465 | A1 | 11/2014 | Herrmann |
| 2014/0328532 | A1* | 11/2014 | Sun ..................... G06T 5/005 |
| | | | 382/131 |
| 2015/0063527 | A1 | 3/2015 | Daerr et al. |
| 2015/0063533 | A1 | 3/2015 | Proksa et al. |
| 2015/0234059 | A1 | 8/2015 | Roessl et al. |
| 2015/0346354 | A1 | 12/2015 | Arakita et al. |
| 2016/0242721 | A1* | 8/2016 | Zou ..................... A61B 6/5205 |
| 2017/0213365 | A1* | 7/2017 | Koehler ................. A61B 6/484 |
| 2018/0182135 | A1* | 6/2018 | Lee ..................... A61B 6/032 |
| 2018/0247434 | A1* | 8/2018 | Qin ..................... G06T 11/003 |

OTHER PUBLICATIONS

Stevens et al., "Simulation of CT Image Noise Impact from Pile-up in Photon Counting Detectors", Radiological Society of North America 2007 Scientific Assembly and Annual Meeting, http://archive.rsna.org/2007/5014364., Abstract is 2 pages, Nov. 2007.

Cammin et al., "Photon-Counting CT: Modeling and Compensating of Spectral Distortion Effects", Physics of Medical Imaging, https://jhu.pure.elsevier.com/en/publications/photon-counting-ct-modeling-and-compensating-of-spectral-distorti-3, Abstract is 3 pages, vol. 9412, 2015.

Jochen et al., "Evaluation of Models of Spectral Distortions in Photon-Counting Detectors for Computed Tomography", J Med Imaging (Bellingham), https://www.ncbi.nlm.nih.gov/pmc/articles/PMC4859407/, 13 pages, Apr. 3, 2016.

* cited by examiner

SYSTEM AND METHOD FOR STATISTICAL ITERATIVE RECONSTRUCTION AND MATERIAL DECOMPOSITION

BACKGROUND

Embodiments of the present specification generally relate to photon-counting computed tomography imaging systems, and more specifically to a system and method for enhancing image quality in photon-counting computed tomography systems via use of a model that incorporates unique statistical properties of X-ray pile-up.

Radiographic imaging systems, such as X-ray and computed tomography (CT) systems have been employed for observing interior aspects of objects. Typically, the imaging systems include an X-ray source that is configured to emit X-rays toward an object of interest, such as a patient, a work piece, a parcel, a piece of luggage, and so forth. A detecting device, such as an array of radiation detectors, is positioned on the opposite side of the object and is configured to detect the X-rays transmitted through the object.

As will be appreciated, a CT scan is conducted by measuring a series of projection measurements from many different angles around a patient or object. These measurements are combined into a sinogram, which collects the projection data from multiple views into a single data set. A reconstruction algorithm is used to process the sinogram to produce an image representing the patient or object. Currently, there exist multiple methods for image reconstruction. In recent years, statistical iterative reconstruction (SIR) methods have been used to produce images of very high quality, while reducing the required radiation dose.

Using the SIR method, the objective is to produce reconstructed images that would result in estimated sinograms that best match a set of measured sinograms collected from a CT scan. On each iteration of the SIR method, the reconstructed image and the known geometry and other characteristics of the CT system are used by a forward model to compute the estimated sinogram that would be produced by the reconstructed image. The forward model essentially simulates the attenuation of X-rays as they pass from the X-ray source, through the patient, as represented by the reconstructed images, and into the detector of the CT system.

Subsequently, the estimated sinogram is compared with the measured sinogram from the CT scan. Based on this comparison, an updated reconstructed image is computed that is configured to make the sinogram estimated by the forward model more similar to the measured sinogram in the subsequent iteration. Typically, the update step is performed as an optimization of an objective function.

Conventional CT and other radiographic imaging systems utilize detectors that convert radiographic energy integrated over a time period into electrical current signals, which are ultimately digitized. A drawback of such detectors however is their inability to provide data or feedback regarding the number and/or energy of detected photons. Energy-discriminating, direct-conversion detectors that are capable of counting X-rays detected during a period of time and providing a measurement of the energy level of each X-ray detected have been employed in prototype CT systems. However, a drawback of these direct-conversion semiconductor detectors is their inability to count at the X-ray photon flux rates typically encountered with conventional CT systems.

Photon-counting CT systems record individual X-ray photons as the photons reach the detector. Disadvantageously, the photon-counting CT systems are unable to efficiently count X-rays that arrive too close together in time. This is typically a problem for measurements at high X-ray flux, and/or in regions of a sinogram including little attenuation through the patient and/or the X-ray source pre-patient filter (bowtie). Certain techniques for a photon-counting CT system to account for pile-up entail correcting the measured sinograms before comparing the estimated sinogram with the measured sinogram.

However, in addition to impacting the number of counts recorded, pile-up also impacts the noise in CT projection data. Noise in projection measurements typically increase with the X-ray flux, following approximately a Poisson distribution. Disadvantageously, when pile-up occurs, both the number of counts and the variation in counts are reduced.

Further, the very high X-ray photon flux rate has been known to cause pile-up and polarization in certain direct-conversion devices that ultimately leads to detector saturation. "Pile-up" is a phenomenon that occurs when X-ray flux incident at the detector is so high that there is a non-negligible possibility that two or more X-ray photons interact with the direct-conversion sensor and deposit charge packets in a single pixel ("photon pile-up"), or in neighboring pixels ("pattern pile-up"), during one charge-integration cycle. In such cases, these events are recognized as one single event having the sum of the individual photon energies. If this happens sufficiently often, a significant distortion of the detected spectrum may result as piled-up events are shifted in the spectrum to higher energies. In addition, pile-up leads to a more or less pronounced depression of efficiency in a projection area including lower attenuation, resulting in flux detection loss. In particular, these detectors typically saturate at relatively low X-ray flux levels. Above these levels, the detector response is less predictable and has degraded dose utilization. That is, once a pixel is saturated (corresponding to higher values in the measured photon counts), additional radiation will not produce useful information in the measurements.

As known in the art, energy-discriminating photon detection systems place X-rays into one or more energy bins. One type of processing of energy bin values called Optimal Energy Weighting (OEW) may enhance the contrast-to-noise ratio relative to a conventional CT system which employs an energy-integration process (the total energy deposited during an acquisition interval is summed). Another type of processing of multiple energy-bin data is called Material Decomposition and is configured to extract quantitative tissue compositional information, if sufficient photon statistics exist, by processing data from multiple energy bins. In particular, photon-counting detectors make it possible to improve image quality and may offer new kinds of tissue compositional information than conventional energy-integrating systems.

Further, as will be appreciated, detector saturation leads to corruption of imaging information and consequently results in noise and artifacts in X-ray projection data and reconstructed CT images. Photon-counting direct-conversion detectors are known to suffer from decreased detector quantum efficiency (DQE) at high count rates mainly due to detector pile-up. In particular, photon-counting direct-conversion detectors incur pile-up due to the intrinsic charge collection time (i.e., dead time) associated with each X-ray photon event. As indicated above, saturation ultimately is often due to pulse pile-up, particularly when the X-ray photon absorption rate for each pixel is on the order of the inverse of this charge collection time. The reciprocal of the charge collection time is called the maximum periodic rate (MPR). When the true mean X-ray count rate incident on the detector is equal to the maximum periodic rate, the recorded counts are one half the input detected counts and the output count rate is only one half the MPR. Reduced DQE results in reduced image quality, i.e., a noisier image. In addition, hysteresis and other non-linear effects occur at flux levels near and above detector saturation and lead to additional image artifacts.

In addition, the relationship between the true signal and the measured signal becomes non-linear, showing a reduction as the count rate is increased. This pile-up effect, if stable, may be calibrated and corrected, thereby increasing the effective count rate capability of the detector, albeit with a penalty of higher noise. However, if the count rate is increased to a point where the relationship between the true signal and the measured signal becomes non-monotonic, which is a characteristic of paralyzable electronics, correction of this non-monotonic relationship may no longer be practical. In particular, when the detector is over-ranged, the recorded count rate may be non-monotonic for increasing flux rate for paralyzable electronics or becomes the maximum achievable count rate for non-paralyzable electronics.

Previously conceived solutions to enable photon counting at high X-ray flux rates include using bowtie shaped filters to pre-condition the flux rate at the detector, compensating for the patient shape. Also, it has been proposed to subdivide the pixel into multiple sub-pixels, each sub-pixel connected to its own preamplifier and associated electronics. By reducing the area of the direct conversion sub-pixel, the flux rate capability may be increased as fewer photons are collected in the smaller area during an acquisition interval. However, the signal-to-noise ratio of the resulting signal may be reduced, and the level of crosstalk, both in terms of photons and deposited charge between neighboring detector pixels may be disadvantageously significant due to the increased perimeter between sub-pixels.

BRIEF DESCRIPTION

In accordance with aspects of the present specification, a method for imaging an object to be reconstructed is presented. The method includes acquiring, via an imaging system, projection data corresponding to the object to be reconstructed. Furthermore, the method includes generating a measured sinogram based on the acquired projection data. Also, the method includes formulating a forward model, where the forward model is representative of a characteristic of the imaging system. In addition, the method includes generating an estimated sinogram based on an estimated image of the object and the forward model. The method also includes formulating a statistical model based on at least one of pile-up characteristics and dead time characteristics of a detector of the imaging system. Moreover, the method includes determining an update corresponding to the estimated image based on the statistical model, the measured sinogram, and the estimated sinogram. Further, the method includes updating the estimated image based on the determined update to generate an updated image of the object. Additionally, the method includes outputting a final image of the object.

In accordance with another aspect of the present specification, a system is presented. The system includes a noise correction platform configured to generate a measured sinogram based on projection data corresponding to an object to be reconstructed, formulate a forward model, where the forward model is representative of one or more characteristics of an imaging system, generate an estimated sinogram based on an estimated image, the forward model, or both the estimated image and the forward model, formulate a statistical model based on at least one of the pile-up characteristics and dead time characteristics of a detector of the imaging system, determine an update corresponding to the estimated image based on the statistical model and the estimated sinogram, update the estimated image based on the determined update to generate an updated image of the object, and output a final image of the object.

In accordance with yet another aspect of the present specification, an imaging system for imaging an object is presented. The system includes an acquisition subsystem configured to acquire projection data corresponding to the object. Moreover, the system includes a processing subsystem in operative association with the acquisition subsystem and including a noise correction platform, where the noise correction platform is configured to generate a measured sinogram based on the projection data corresponding to the object, formulate a forward model, where the forward model is representative of a characteristic of the imaging system, generate an estimated sinogram based on an estimated image, the forward model, or both the estimated image and the forward model, formulate a statistical model based on at least one of pile-up characteristics and dead time characteristics of a detector of the imaging system, determine an update corresponding to the estimated image based on the statistical model and the estimated sinogram, update the estimated image based on the determined update to generate an updated image of the object, and output a final image of the object. Additionally, the system includes a display configured to visualize at least one of the final image, the updated image, the measured sinogram, the estimated sinogram, or combinations thereof.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
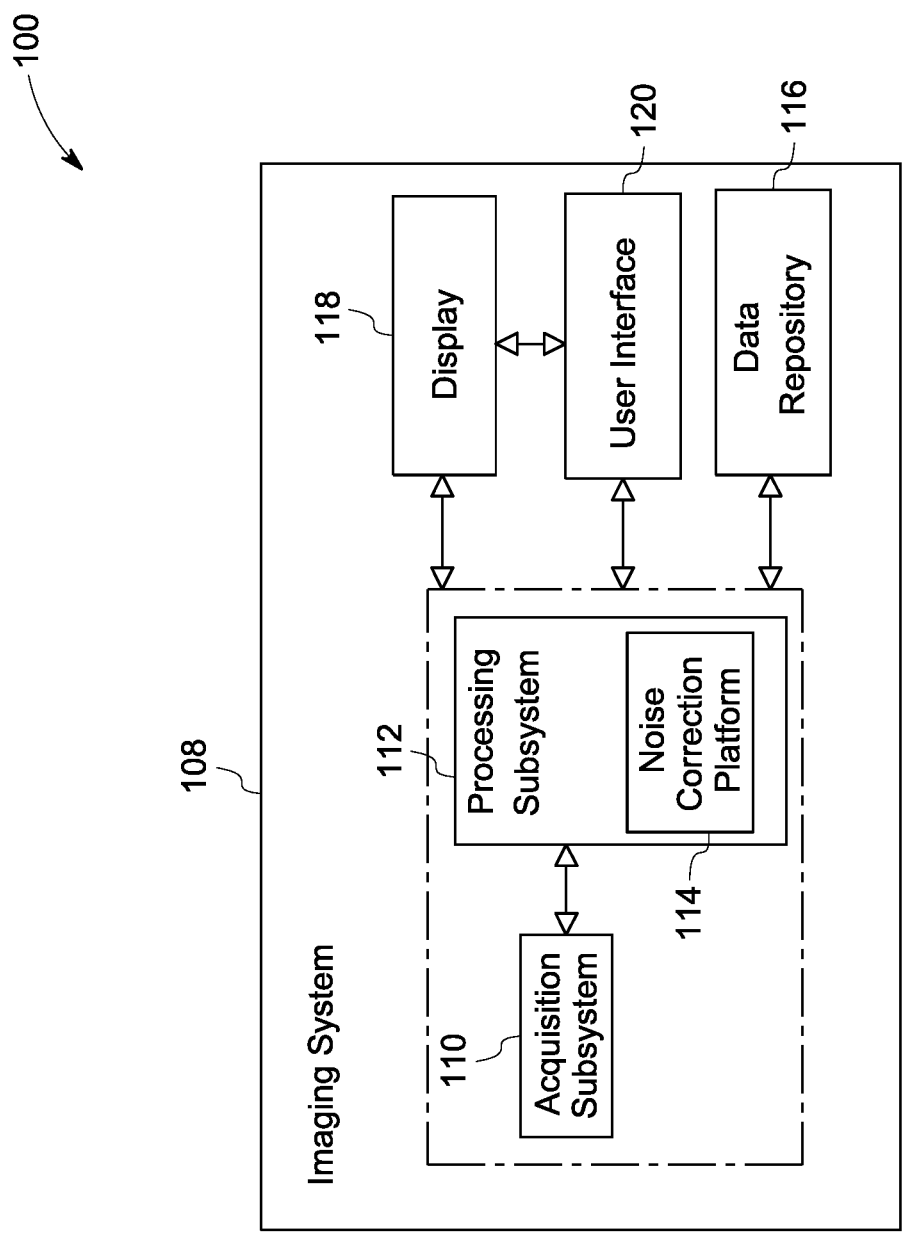
FIG. 1 is a diagrammatical illustration of a system for imaging, in accordance with aspects of the present specification.
Figure 1:
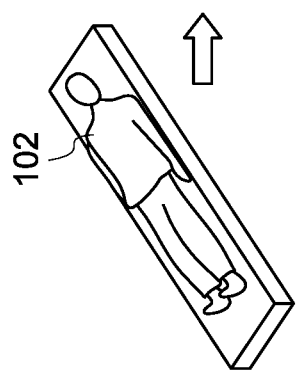

As will be appreciated, during imaging an object of interest using photon-counting computed tomography (PCCT), individual X-ray photons are detected and recorded as they interact with the detector. However, the PCCT systems may suffer from imperfect counting of X-rays that arrive too close together in time. This is typically a problem for measurements at high X-ray flux, and/or regions of a sinogram with little attenuation through the patient and/or the X-ray source pre-patient filter (bowtie). There is therefore a need for a design that advantageously combines information from a photon-counting detector in an optimal way, taking into account associated noise in order to extend the flux rate capability and allow efficient photon counting in medical and industrial applications that are heretofore unmanageable because either the incident flux rate or the dynamic range requirements are too high. Additionally, there is a particular need for correction algorithms for known deleterious effects, such as pile-up and pixel over-range. There is also a need for a CT system that enhances image quality and provides sufficient photon-count statistics in one or more energy bins to ensure statistically-significant tissue compositional information.

As will be described in detail hereinafter, various embodiments of systems and methods for statistical iterative reconstruction and/or material decomposition are presented. The systems and methods presented herein entail use of a noise model, where unique statistical properties of X-ray pile-up are incorporated into the noise model of an iterative algorithm for statistical image reconstruction or material decomposition for PCCT imaging. In particular, the exemplary noise model of statistical behavior of a detector with pile-up is incorporated into an objective function in an optimization step of the iterative algorithm, thereby performing at least of one of optimizing the noise and reducing artifacts in a reconstructed image by accounting for statistical uncertainty in respective measurements. It may be noted that the terms "noise model," "statistical model," and "statistical noise model" may be used interchangeably.

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect. Furthermore, the terms "circuit" and "circuitry" and "controller" may include either a single component or a plurality of components, which are either active and/or passive and are connected or otherwise coupled together to provide the described function.

For clarity, exemplary embodiments of the present systems and methods are described in the context of a computed tomography (CT) imaging system. However, it will be appreciated that use of the present systems and methods in various other imaging applications and systems is also contemplated. Some of these systems, for example, may include a single photon emission computed tomography (SPECT) system, a positron emission tomography (PET) system, an X-ray imaging system, and/or an optical imaging system. An exemplary environment that is suitable for practicing various implementations of the present system and methods is discussed in the following sections with reference to FIGS. 1-3.

Turning now to the drawings, FIG. 1 is a block diagram of an exemplary system 100 for use in diagnostic imaging, in accordance with aspects of the present specification. In particular, the system 100 is configured to generate one or more images corresponding to an object to be reconstructed. By way of example, the system 100 may be configured to generate images corresponding to a target volume and/or internal structures of an object 102 such as a patient/subject or a non-biological object. More specifically, the system 100 is configured to enhance the quality of imaging via use of a noise model with an iterative algorithm for statistical image reconstruction or material decomposition.

The system 100 is configured to acquire image data corresponding to an object to be reconstructed such as a patient 102. In one example, the system 100 includes a medical imaging system 108 configured to acquire projection data for use in generating desired images of the patient 102. It should be noted that although the exemplary embodiments illustrated hereinafter are described in the context of a medical imaging system, other imaging systems and applications such as industrial imaging systems and non-destructive evaluation and inspection systems; such as pipeline inspection systems, explosives detection system, and liquid reactor inspection systems; are also contemplated. Additionally, the exemplary embodiments illustrated and described hereinafter may find application in multi-modality imaging systems that employ CT imaging in conjunction with other imaging modalities, for example, SPECT, PET, X-ray, optical imaging systems, position-tracking systems, or other sensor systems.

In a presently contemplated configuration, the medical imaging system 108 includes an acquisition subsystem 110 and a processing subsystem 112. The acquisition subsystem 110 of the medical imaging system 108 is configured to acquire projection data representative of one or more anatomical regions of interest in the patient 102. It may be noted that the data acquisition subsystem 110 measures photon counts detected in one or more energy bins during one or more acquisition intervals. This data may be transferred directly to processing subsystem 112 or processed further before being transferred to processing subsystem 112. For example, the detected photon counts may be processed to generate projection data corresponding to line integrals of the linear attenuation coefficients of materials positioned between the X-ray source and detector element. It may be noted that the data including both detected counts and/or processed detected counts is collectively referred to as projection data. Further, the projection data acquired from the patient 102 is processed by the processing subsystem 112 to generate images corresponding to the anatomical regions of interest in the patient 102.

The processing subsystem 112, for example, may include one or more application-specific processors, graphical processing units, digital signal processors, microcomputers, microcontrollers, Application Specific Integrated Circuits (ASICs), Field Programmable Gate Arrays (FPGAs), Programmable Logic Arrays (PLAs), and/or other suitable processing devices. Additionally or alternatively, the processing subsystem 112 may be configured to store the acquired projection data and/or the user input in a data repository 116 for later use. In one embodiment, the data repository 116, for example, may include a hard disk drive, a floppy disk drive, a compact disk-read/write (CD-R/W) drive, a Digital Versatile Disc (DVD) drive, a flash drive, and/or a solid-state storage device.

In certain embodiments, the processing subsystem 112 may be configured to retrieve the projection data and/or any user input from the data repository 116 for reconstructing images of a target volume corresponding to the patient 102. Additionally or optionally, in one embodiment, the processing subsystem 112 may be configured to pre-process the acquired projection data for reconstruction and/or motion-correction based on specific physical principles employed by the system 100 for imaging the target volume. For example, if the system medical imaging system 108 corresponds to a CT imaging system, the processing subsystem 116 may be configured to perform dynamic range normalization to produce Hounsfield Units in reconstructing desired images of the target volume.

As will be appreciated, a drawback of detectors that are used in conventional photon-counting imaging systems is their inability to count at the X-ray photon flux rates typically encountered with CT systems. In particular, pile-up and polarization caused by very high X-ray photon flux rate lead to detector saturation, flux loss, and unpredictable behavior of the detectors. Moreover, detector saturation leads to loss of imaging information and consequently results in noise and artifacts in X-ray projection and CT images. Photon-counting direct-conversion detectors may to suffer from decreased detector quantum efficiency (DQE) at high count rates mainly due to detector pile-up, thereby resulting in reduced image quality, i.e., a noisier image. In addition, hysteresis and other non-linear effects occur at flux levels near detector saturation as well as flux levels over detector saturation, leading to image artifacts.

In accordance with exemplary aspects of the present specification, the processing subsystem 112 may include a noise correction platform 114 that is configured to aid in the correction of known deleterious effects, such as pile-up and pixel over-range. More particularly, the noise correction platform 114 is configured to facilitate reduction of noise in reconstructed images. Specifically, the noise correction platform 114 is configured to process the acquired projection data via a noise model that incorporates the statistical properties of noise, thereby facilitating reduction in noise in the reconstructed images. The exemplary noise correction platform 114 is configured to generate a measured sinogram based on projection data corresponding to an object, formulate a forward model, where the forward model is representative of a behavior/one or more characteristics of an imaging system, generate an estimated sinogram based on an estimated image, the forward model, or both the estimated image and the forward model, formulate a statistical model based on pile-up characteristics and dead time characteristics of a detector of the imaging system, determine an image update corresponding to the estimated image based on the statistical model and the estimated sinogram, update the estimated image based on the determined update to generate an updated image having reduced noise, and output at least a final image of the object/patient 102. The final image of the object may include a final reconstructed image of the patient 102. Also, in one example, the final reconstructed image may be output in the form of a visualization on a display such as a display 118. In certain embodiments, the final reconstructed image may include monochromatic energy images or basis material images. The noise correction platform 114 will be described in greater detail with reference to FIGS. 4-13.

Also, in the presently contemplated configuration illustrated in FIG. 1, the processing subsystem 112 is shown as including the noise correction platform 114. However, in certain embodiments, the noise correction platform 114 may also be used as a standalone unit that is physically separate from the processing subsystem 112 and the medical imaging system 108. By way of example, the noise correction platform 114 may be external to and operatively coupled to the medical imaging system 108.

In certain embodiments, the processing subsystem 112 may be further coupled to a storage system, such as the data repository 116. The data repository 116 is configured to receive and/or store image data.

Further, as illustrated in FIG. 1, the medical imaging system 108 may include the display 118 and a user interface 120. However, in certain embodiments, such as in a touch screen, the display 118 and the user interface 120 may overlap. Also, in some embodiments, the display 118 and the user interface 120 may include a common area. In accordance with aspects of the present specification, the display 118 of the medical imaging system 108 may be configured to display an image generated by the medical imaging system 108 based on the projection data that has been acquired and processed by the noise correction platform 114. Additionally, the reconstructed images generated by the medical imaging system 108 may be employed to aid a clinician in identifying disease states, assessing need for treatment, determining suitable treatment options, and/or monitoring the effect of treatment on the disease states. It may be noted that the terms treatment and therapy may be used interchangeably.

In addition, the user interface 120 of the medical imaging system 108 may include a human interface device (not shown) configured to facilitate the clinician in manipulating image data displayed on the display 118. The human interface device may include a mouse-type device, a trackball, a joystick, a stylus, or a touch screen configured to facilitate the clinician to identify one or more regions of interest requiring therapy. However, as will be appreciated, other human interface devices, such as, but not limited to, a touch screen, may also be employed. Furthermore, in accordance with aspects of the present specification, the user interface 120 may be configured to aid the clinician in navigating through the images generated by the medical imaging system 108.

As previously noted with reference to FIG. 1, the medical imaging system 108 may include a CT imaging system. FIG.

2 is a block diagram showing an imaging system 200 for acquiring and processing image data, in accordance with the present specification. In the illustrated embodiment, the system 200 is a CT imaging system designed to acquire X-ray projection data, to reconstruct the projection data into an image, and to process the image data for display and analysis in accordance with the present specification. In the embodiment illustrated in FIG. 2, the imaging system 200 includes a source of X-ray radiation 202. In one embodiment, the source of X-ray radiation 200 may include an X-ray tube. The source of X-ray radiation 202 may include thermionic or solid-state electron emitters directed at an anode to generate X-rays or, indeed, any other emitter capable of generating X-rays having a spectrum and energy useful for imaging a desired object. Examples of suitable electron emitters include tungsten filament, tungsten plate, field emitter, thermal field emitter, dispenser cathode, thermionic cathode, photo-emitter, and ferroelectric cathode.

The source of radiation 202 may be positioned near a collimator 204, which may be configured to shape a stream of radiation 206 that is emitted by the source of radiation 202. The stream of radiation 206 passes into the imaging volume containing a subject 208 to be imaged, such as the patient 102 (see FIG. 1). The stream of radiation 206 may be generally fan-shaped or cone-shaped, depending on the configuration of the detector array as well as the desired method of data acquisition. A portion 210 of radiation passes through or around the subject 208 and impacts a detector array, represented generally by reference numeral 212. Detector elements of the detector or detector array 212 produce electrical signals that represent the intensity of the incident X-ray beam or the counts of photons detected during an acquisition interval in one or more energy bins. These signals are acquired and processed to reconstruct an image of the features within the subject 208.

The radiation source 202 is controlled by a system controller 214, which furnishes both power and control signals for CT examination sequences. Moreover, the detector 212 is coupled to the system controller 214, which commands acquisition of the signals generated in the detector 212. The system controller 214 may also execute various signal processing and filtration functions, such as for initial adjustment of dynamic ranges, interleaving of digital image data, and so forth. In general, the system controller 214 commands operation of the imaging system 200 to execute examination protocols and to process acquired data. In the present context, the system controller 214 also includes signal processing circuitry, typically based upon a general purpose or application-specific digital computer, associated memory circuitry for storing programs and routines executed by the computer, as well as configuration parameters and image data, interface circuits, and so forth.

Figure 2:
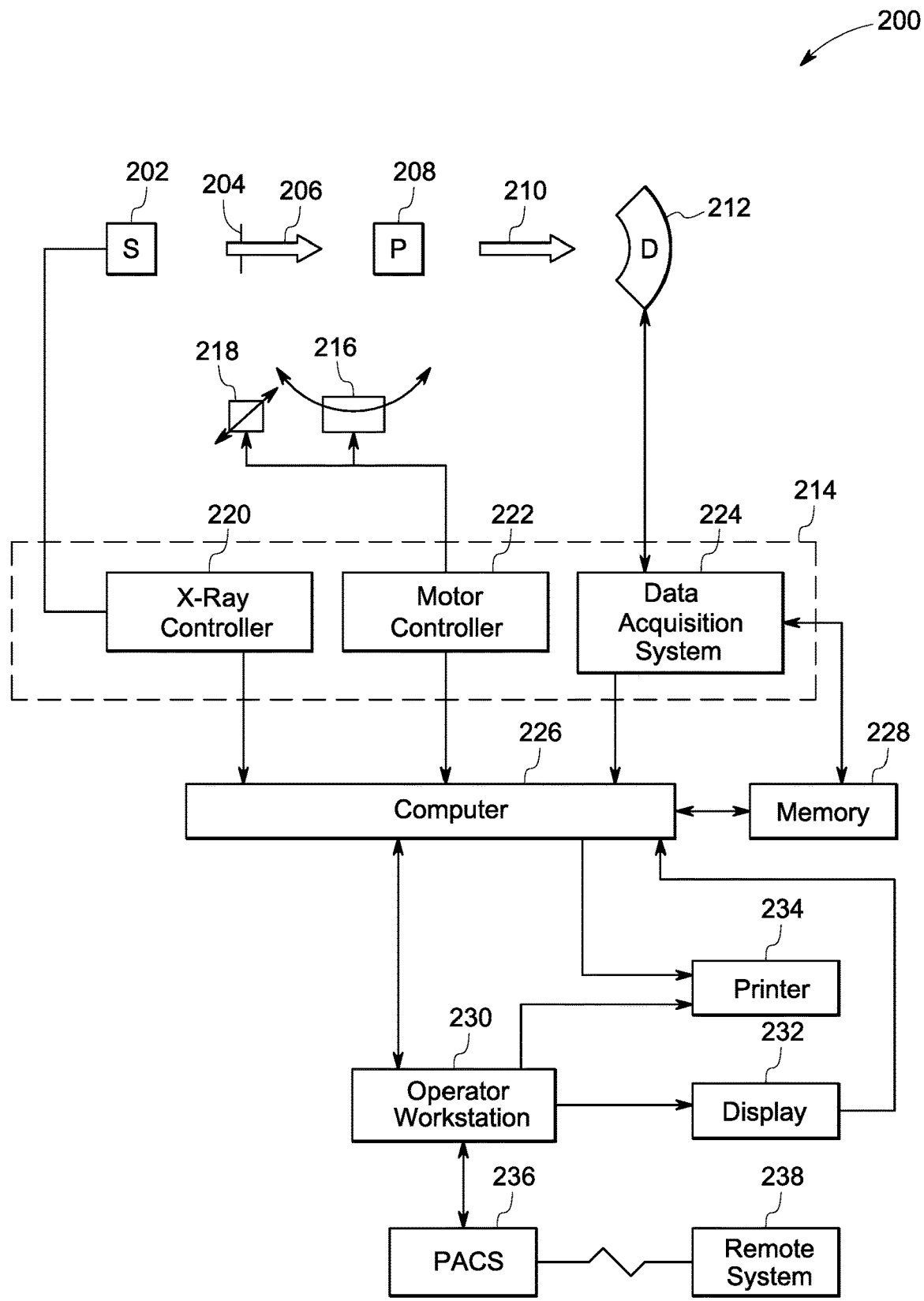
FIG. 2 is a block diagram of an exemplary imaging system in the form of a CT imaging system for use in the exemplary system of FIG. 1.

In the embodiment illustrated in FIG. 2, the system controller 214 is coupled via a motor controller 222 to a rotational subsystem 216 and a linear positioning subsystem 218. In one embodiment, the rotational subsystem 216 enables the X-ray source 202, the collimator 204, and the detector 212 to be rotated one or multiple turns around the patient 208. In other embodiments, the rotational subsystem 216 may rotate only one of the source 202 or the detector 212 or may differentially activate various stationary electron emitters to generate X-ray radiation and/or detector elements arranged in a ring about the imaging volume. In embodiments in which the source 202 and/or detector 212 are rotated, the rotational subsystem 216 may include a gantry (not shown in FIG. 2). Thus, the system controller 214 may be utilized to operate the gantry. The linear positioning subsystem 218 enables the patient 208, or more specifically a patient table (not shown in FIG. 2), to be displaced linearly. Thus, the patient table may be linearly moved within the gantry to generate images of particular areas of the patient 208.

Additionally, as will be appreciated by one skilled in the art, the source of radiation 202 may be controlled by an X-ray controller 220 disposed within the system controller 214. Particularly, the X-ray controller 220 is configured to provide power and timing signals to the X-ray source 202.

Further, the system controller 214 is also illustrated as including a data acquisition system 224. In this embodiment, the detector 212 is coupled to the system controller 214, and more particularly to the data acquisition system 224. The data acquisition system 224 receives data collected by readout electronics of the detector 212. The data acquisition system 224 typically receives sampled analog signals from the detector 212 and converts the data to digital signals for subsequent processing by a computer 226.

The computer 226 typically is coupled to or incorporates the system controller 214. The data collected by the data acquisition system 224 may be transmitted to the computer 226 for subsequent processing and reconstruction. The computer 226 may include or communicate with a memory 228 that may store data processed by the computer 226 or data to be processed by the computer 226. It may be noted that any type of memory configured to store a large amount of data might be utilized by the system 200. Moreover, the memory 228 may be located at the acquisition system or may include remote components, such as network accessible memory media, for storing data, processing parameters, and/or routines for implementing the techniques described hereinafter.

The computer 226 may also be adapted to control features such as scanning operations and data acquisition that may be enabled by the system controller 214. Furthermore, the computer 226 may be configured to receive commands and scanning parameters from an operator via an operator workstation 230, which is typically equipped with a keyboard and other input devices (not shown). It may be noted that the operator workstation 230 may include the user interface 120 (see FIG. 1), in certain embodiments. An operator, such as a clinician or technician, may thereby control the system 200 via the input devices. Thus, the clinician or technician may observe the reconstructed image and other data relevant to the system 200 from the computer 226, initiate imaging, and so forth.

A display 232 coupled to the operator workstation 230 may be utilized to observe the reconstructed images. It may be noted that the display 232 may be the display 118 (see FIG. 1), in certain embodiments. Additionally, the scanned image may also be printed by a printer 234, which may be coupled to the operator workstation 230. The display 232 and the printer 234 may also be connected to the computer 226, either directly or via the operator workstation 230. The operator workstation 230 may also be coupled to a picture archiving and communications system (PACS) 236. It should be noted that PACS 236 might be coupled to a remote system 238, such as radiology department information system (RIS), hospital information system (HIS), or to an internal or external network, so that other clinicians at different locations may gain access to the image data.

It should be further noted that the computer 226 and the operator workstation 230 may be coupled to other output devices, which may include standard or special purpose computer monitors and associated processing circuitry. One or more operator workstations 230 may be further linked in the system for outputting system parameters, requesting examinations, viewing images, and so forth. In general, displays, printers, workstations, and similar devices supplied within the system 200 may be local to the data acquisition components, or may be remote from these components, such as elsewhere within an institution or hospital, or in an entirely different location, linked to the image acquisition system via one or more configurable networks, such as the Internet, a virtual private network, or the like.

As noted hereinabove, an exemplary imaging system utilized in a present embodiment may be a CT scanning system 300, as depicted in greater detail in FIG. 3. The CT scanning system 300 may be a multi-slice CT (MSCT) system that offers a wide array of axial coverage, high rotational speed of the gantry, and high spatial resolution. Alternatively, the CT scanning system 300 may be a volumetric CT (VCT) system utilizing a cone-beam geometry and an area detector to allow the imaging of a volume, such as an entire internal organ of a subject, at high or low gantry rotational speeds. The CT scanning system 300 is illustrated with a frame 302 and a gantry 304 that has an aperture 306 through which a patient such as the patient 102 (see FIG. 1) may be moved. A patient table 308 may be positioned in the aperture 306 of the frame 302 and the gantry 304 to facilitate movement of the patient 102, typically via linear displacement of the table 308 by the linear positioning subsystem 218 (see FIG. 2). The gantry 304 is illustrated with the source of radiation 310, such as an X-ray tube that emits X-ray radiation from one or more focal points 312. In the example of cardiac imaging, the stream of radiation is directed towards a cross section of the patient 102 including the heart.

In typical operation, the X-ray source 310 projects an X-ray beam from the focal point 312 and toward a detector array 314. The collimator 204 (see FIG. 2), such as lead or tungsten shutters, typically defines the size and shape of the X-ray beam that emerges from the X-ray source 310. The detector 314 is generally formed by a plurality of detector elements, which detect the X-rays that pass through and around a region of interest in the patient 102, such as the heart or chest. Each detector element produces an electrical signal that represents the intensity of the X-ray beam at the position of the element during the time the beam strikes the detector. Alternatively, in an energy-discriminating, photon-counting CT system, each detector element produces a count of detected photons during an acquisition interval in one or more energy bins. The gantry 304 is rotated around the patient 102 of interest so that a plurality of radiographic views may be collected by the computer 226 (see FIG. 2).

Thus, as the X-ray source 310 and the detector 314 rotate, the detector 314 collects data related to the attenuated X-ray beams. Data collected from the detector 314 then undergoes pre-processing and calibration to condition the data to represent the line integrals of the attenuation coefficients of the scanned objects. The processed data, commonly called projections or projection data, may then be filtered and backprojected to formulate an image of the scanned area. A formulated image may incorporate, in certain modes, projection data for less or more than 360 degrees of rotation of the gantry 304.

Figure 3:
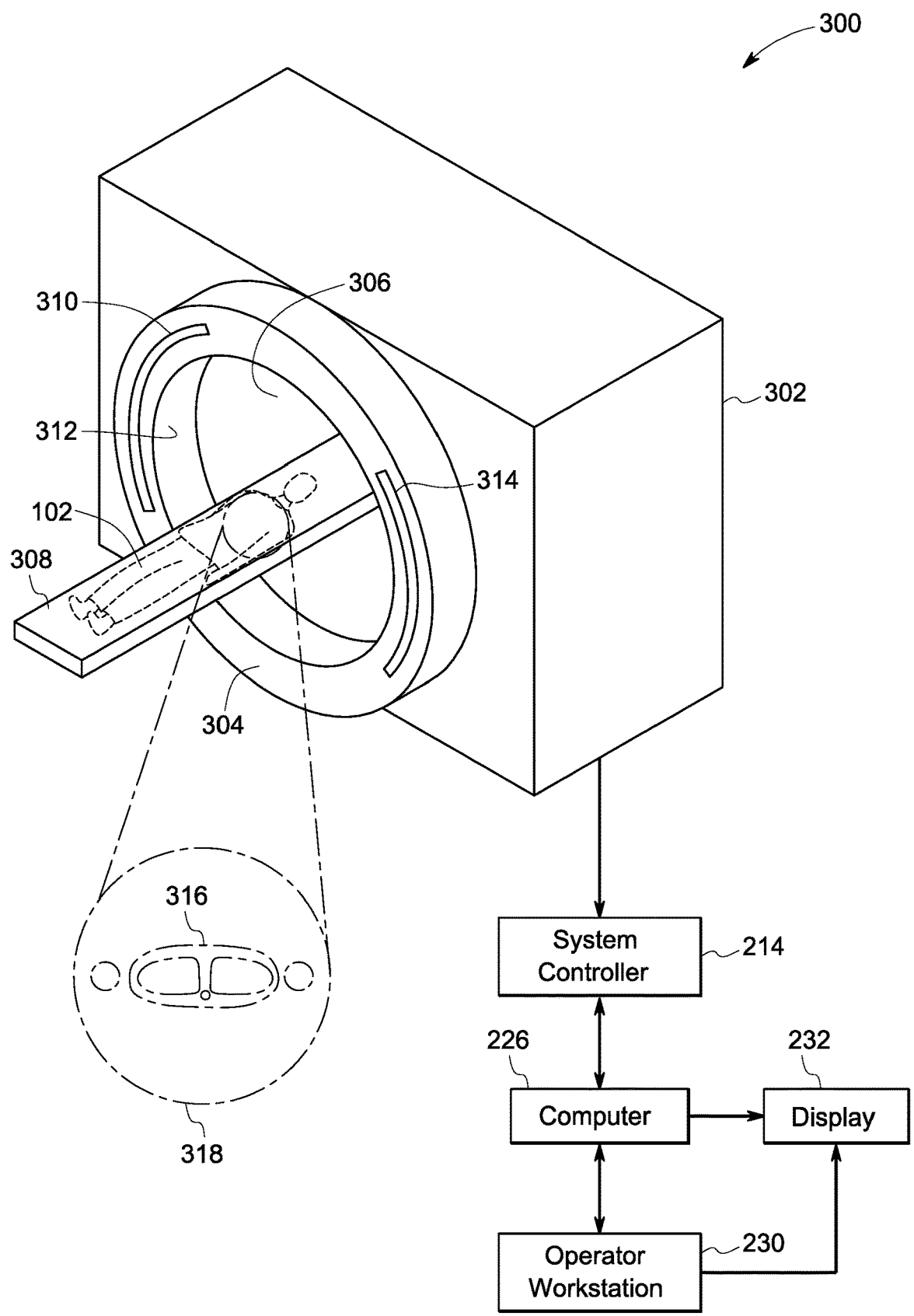
FIG. 3 is a block diagram of a physical implementation of the CT system of FIG. 2.

Once reconstructed, the image produced by the systems of FIGS. 2-3 reveals internal features 316 of the patient 102. In traditional approaches for the diagnosis of disease states, and more generally of medical conditions or events, a radiologist or physician typically consider a reconstructed image 318 to discern characteristic features of interest. In cardiac imaging, such features 316 include coronary arteries or stenotic lesions of interest, and other features, which would be discernable in the image, based upon the skill and knowledge of the individual practitioner. Other analyses may be based upon capabilities of various algorithms, including algorithms generally referred to as computer-aided detection or computer-aided diagnosis (CAD) algorithms.

The working of the system 100 (see FIG. 1) and the noise correction platform 114 (see FIG. 1) in particular may be better understood with reference to the exemplary logic depicted in FIGS. 4-11.

In the present specification, embodiments of exemplary methods of FIGS. 4-11 may be described in a general context of computer executable instructions on a computing system or a processor. Generally, computer executable instructions may include routines, programs, objects, components, data structures, procedures, modules, functions, and the like that perform particular functions or implement particular abstract data types.

Additionally, embodiments of the exemplary methods of FIGS. 4-11 may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIGS. 4-11, the exemplary methods are illustrated as a collection of blocks in a logical flow chart, which represents operations that may be implemented in hardware, software, or combinations thereof. The various operations are depicted in the blocks to illustrate the functions that are performed. In the context of software, the blocks represent computer instructions that, when executed by one or more processing subsystems, perform the recited operations.

The order in which the exemplary methods of FIGS. 4-11 are described is not intended to be construed as a limitation, and any number of the described blocks may be combined in any order to implement the exemplary methods disclosed herein, or equivalent alternative methods. Additionally, certain blocks may be deleted from the exemplary methods or augmented by additional blocks with added functionality without departing from the spirit and scope of the subject matter described herein. Although, the exemplary embodiments illustrated hereinafter are described in the context of a medical imaging system, it will be appreciated that use of the systems and methods in industrial applications is also contemplated in conjunction with the present specification.

Figure 4:
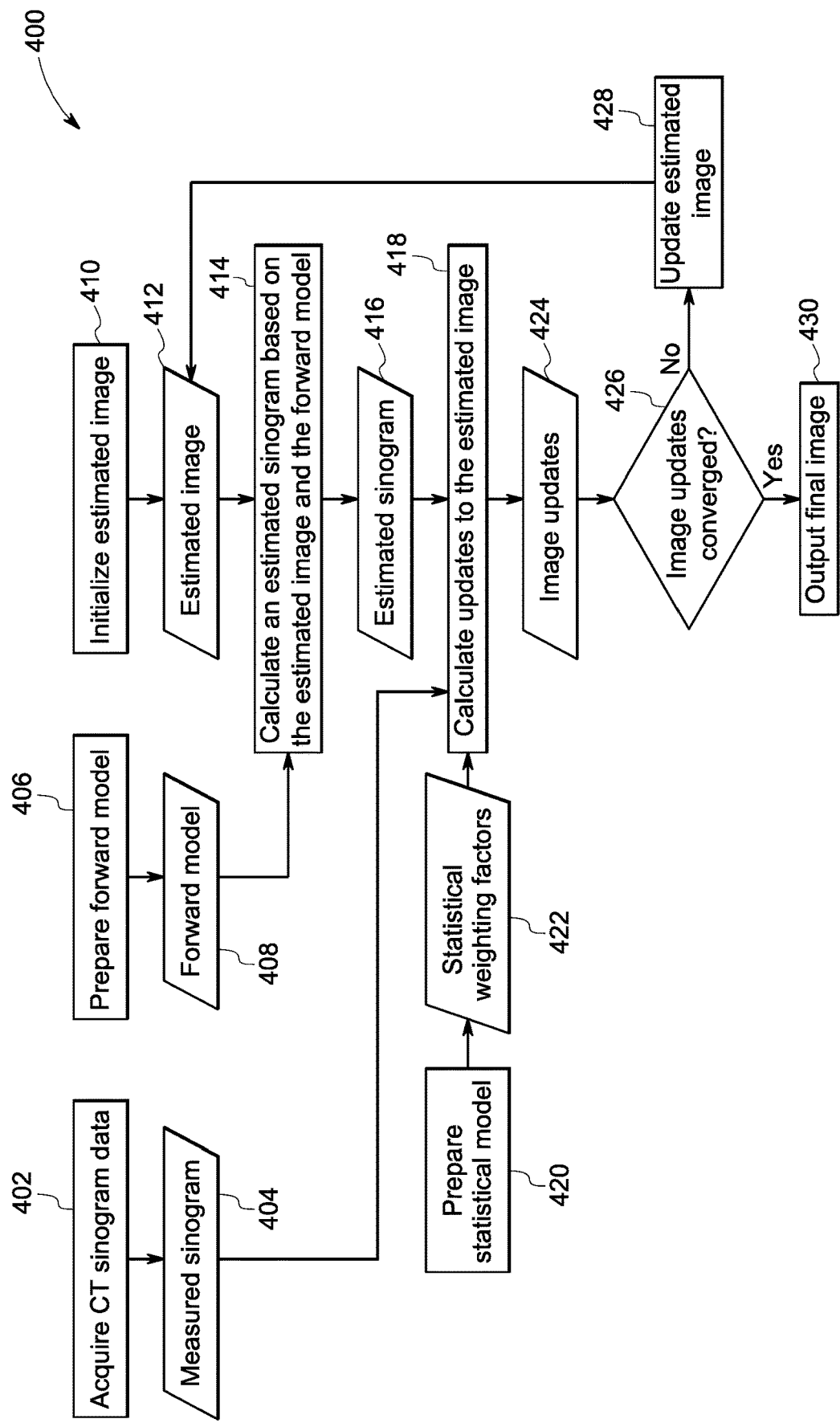
FIG. 4 is a flow chart of a method of imaging, in accordance with aspects of the present specification.

Referring now to FIG. 4, a flow chart of exemplary logic 400 for a method of imaging is illustrated. In accordance with exemplary aspects of the present specification, a method for enhancing image quality in PCCT systems via use of a model that incorporates unique statistical properties of X-ray pile-up is presented. The method 400 is described with reference to the components of FIGS. 1-3. Also, in certain embodiments, the noise correction platform 114 may be employed to perform the steps of the method 400.

The method starts at step 402, where a CT scan of a patient such as the patient 102, 208 is performed where CT projection data corresponding to one or more anatomical regions of interest in the patient 208 is acquired. By way of example, the medical imaging system 200 is configured to acquire X-ray attenuation data, where the X-ray attenuation data is used for processing and/or reconstruction. The acquired projection data is representative of data corresponding to a target region in a subject such as the patient 208. It may be noted that the X-ray source 202, 310 may be an X-ray tube, a distributed X-ray source (such as a solid-state or thermionic X-ray source) or any other source of X-ray radiation suitable for the acquisition of medical or other images. The X-rays 206 generated by the source 202 traverse a region in which the patient 208 is positioned during an imaging or diagnostic procedure. In one example, the X-rays 206 may be collimated via that collimator 204 to form the beam 206. This beam 206 may pass through the imaged volume. The portion 210 of the X-ray radiation 206 passes through or around the patient 208 (or another subject of interest) and impacts the detector array, represented generally as the detector 212. Detector elements of the detector 212 produce electrical signals that represent the intensity of the portion of the incident X-rays 210. These signals are acquired and processed to represent images of the features within the patient 208. Also, these images are generally referred to as "projection images" or "projection views," and correspond to projection data acquired at many different rotational angles of the X-ray source 202 and detector 212 relative to the patient 208. Conversely, in an industrial CT system, the X-ray source 202 and detector 212 are held fixed, and the object is rotated to generate the projection views. Moreover, these projection images are combined into a sinogram, where the sinogram collects the multiple views into a single data set. Reference numeral 404 generally represents measured sinogram data acquired at step 402.

Furthermore, at step 406, a forward model 408 is formulated or generated. In particular, the forward model 408 is representative of a behavior or one or more characteristics of the imaging system 100, 200. Specifically, during each iteration of a statistical iterative reconstruction (SIR) algorithm, the forward model 408 is employed to process the reconstructed image to generate an estimated sinogram.

Accordingly, the imaging system 100, 200, and more particularly, the noise correction platform 114 is configured to acquire pile-up characteristics and dead time characteristics of the detector 212 of the imaging system 200. Additionally, the noise correction platform 114 is also configured to acquire system characteristics of the imaging system 200. In one embodiment, the forward model 408 is generated by modeling a behavior of the imaging system 100, 200 based on the system characteristics. The formulation of this embodiment of the forward model 408 will be described in greater detail with reference to FIG. 6. In certain other embodiments, the forward model 408 is generated by modeling, for example, a behavior of the imaging system 100, 200 based on pile-up characteristics, dead time characteristics, system characteristics, measured system behavior, or combinations thereof. The formulation of this embodiment of the forward model 408 will be described in greater detail with reference to FIG. 7.

Moreover, an estimated image may be initialized, as indicated by step 410. In one embodiment, the estimated image may be initialized by setting all pixels to "1." In other embodiments, a filtered back projection image may be used to initialize the estimated image. Reference numeral 412 may be generally representative of the estimated image. Subsequently, at step 414, an estimated sinogram 416 is generated based on the estimated image 412 and the forward model 408.

As will be appreciated, the estimated sinogram 416 is employed to generate a reconstructed image. In a SIR process, it is desirable that the resulting reconstructed image when the reconstruction is complete is a high-quality image. Accordingly, it is desirable that the estimated sinogram 416 be directly comparable to the measured sinogram 404 to facilitate the generation of a high-quality reconstructed image. Hence, the estimated sinogram 416 is compared with the measured sinogram 404. Based on this comparison, it may be desirable to compute an updated estimated/reconstructed image that will aid in making the estimated sinogram 416 more similar to the measured sinogram 404 in a subsequent iteration.

Accordingly, as indicated by step 418, one or more image updates 424 to the estimated image 412 are calculated. To that end, the estimated sinogram 416 is compared to the measured sinogram 404. In particular, a statistically-weighted difference between the estimated sinogram 416 and the measured sinogram 404 is determined. In one embodiment, a statistical model is employed to determine the statistically-weighted difference between the estimated sinogram 416 and the measured sinogram 404. Subsequently, an update to the estimated image 412 is computed based on the statistically-weighted difference between the estimated sinogram 416 and the measured sinogram 404.

As noted hereinabove, a statistical model is employed to determine the statistically-weighted difference between the estimated sinogram 416 and the measured sinogram 404. Accordingly, a statistical noise model is generated, as indicated by step 420. In one embodiment, the statistical noise model is generated based on applied X-ray intensity 206 and the statistical behavior of the detector 212 of the imaging system 200. In certain examples, the statistical model is generated based on the pile-up characteristics and the dead time characteristics of the detector with pile-up. Furthermore, the statistical model may be based on the pulse response(s) of the detector 212.

Moreover, in certain embodiments, at least one parameter of the statistical model is estimated based on detector measurements corresponding to two or more neighboring detector channels, detector measurements corresponding to two or more energy bins, or a combination thereof. In certain other embodiments, at least one parameter of the statistical model maybe iteratively estimated. Also, in yet another embodiment, at least one parameter of the statistical model may be estimated based on a denoising technique, a variance reduction technique, a deep neural network, or combinations thereof.

As will be appreciated, in an iterative process, a sinogram is estimated and compared to a measured sinogram. Additionally, weights are used to decide how to update the images based on differences between the estimated sinogram and the measured sinogram. In particular, the differences between the estimated and measured sinograms are not all equally important. A pixel with high counts has a higher signal-to-noise ratio than a pixel with low counts. Accordingly, the high count pixel is more important to the image. Hence, the high count pixel is accorded a higher weight in the comparison. Specifically, the statistical model is employed to determine how much weight each pixel needs to be accorded. Moreover, in the presence of pile-up, the noise model ceases to be a Poisson distribution. It is therefore desirable to calculate the correct noise for a given number of counts measured based on the pile-up behavior of a particular detector.

In accordance with aspects of the present specification, the statistical model is configured to provide correction in the mean and variance of measured counts of the detector 212. It may also be noted that the noise is modeled as a correction to the conventional Binomial noise, Poisson noise, or Gaussian noise.

Also, the statistical noise model includes one or more statistical weighting factors 422. These statistical weighting factors 422 are employed to determine the statistically-weighted difference between the estimated sinogram 416 and the measured sinogram 404. The generation of the statistical model of step 420 will be described in greater detail with reference to FIGS. 8-10.

Furthermore, in accordance with aspects of the present specification, the unique statistical properties of X-ray pile-up are incorporated into the statistical noise model of an iterative algorithm for statistical image reconstruction or material decomposition for PCCT imaging. In particular, the exemplary noise model of statistical behavior of a detector with pile-up is incorporated into an objective function in an optimization step of the SIR algorithm, thereby performing at least one of optimizing the noise and reducing artifacts in the reconstructed image. The step of determining the update (s) is typically performed as an optimization of an objective function for example, a weighted least squares cost function or a log-likelihood function. It may be noted that more closely the estimated sinogram 416 matches the measured sinogram 404, the objective function is approaching its optimum.

In certain embodiments, the statistical weighting factors 422 may be included with a set of weighting factors that is used in calculating the objective function. These weights represent different features by which the model and measurements may be compared with each other. By incorporating different factors into the cost function and optimizing the weight factors, the resulting image may be optimized to produce the desired image quality. Incorporating the statistical noise model into the objective function during the optimization step emulates the effect of at least one of optimizing noise and reducing artifacts in the reconstructed image by accounting for the statistical uncertainty in respective measurements. Furthermore, in one embodiment, the pile-up correction may be applied to the measured sinogram 404. In other embodiments, the pile-up correction may be incorporated directly into the forward model 408. In an alternative embodiment, the statistical weighting factors 422 may be replaced by weights that relate to the fidelity of the data. For example, the weights may be indicative of the amount of pile-up in the measurements—lower weights for higher amounts of pile-up and higher weights for lower amounts of pile-up.

Prior to the processing of step 418 via the statistical noise model or statistical weighting factors 422, one or more image updates 424 are generated. As noted hereinabove, the image update(s) 424 are determined based on the statistically-weighted difference between the estimated sinogram 416 and the measured sinogram 404. Determining the image updates 424 will be described in greater detail with reference to FIG. 11.

Once the image updates 424 are determined, the estimated image 412 is updated based on the determined update(s) 424 to generate an updated estimated image. Prior to updating the estimated image, a check is carried out to verify if the determined image update 424 has converged, as indicated by step 426. In one example, convergence of the image update 424 may be verified by comparing the determined image update 424 or functionals thereof with a determined threshold.

At step 426, if it is determined that the image update 424 has not converged, then the estimated image 412 is updated via use of the determined image update 424 to generate an updated estimated image, as indicated by step 428. Control is then passed to step 414.

Steps 414-428 may be iteratively repeated until the determined image update 424 has converged. It may be noted that in a first iteration, the estimated image 412 serves as an input to the iterative process of steps 414-428, and the updated estimated image is generated as an output to the iterative process of steps 414-428. Accordingly, for a subsequent iteration, the updated estimated image serves as an input to the iterative process of steps 414-428.

However, at step 426, if it is determined that the image update 424 has converged, the estimated image 412 is not updated. Also, at step 430, the estimated image 412 may be output as a final reconstructed image. In one example, the final reconstructed image may be visualized on a display such as the display 118 of FIG. 1. The estimated image so generated is representative of a final reconstructed image that presents the best match of the estimated sinogram 416 with the measured sinogram 404. In addition, this reconstructed image represents an image of enhanced quality where the effects of noise and/or image artifacts have been optimized/reduced via use of the exemplary statistical noise model. A clinician may use this reconstructed image to provide a diagnosis to the patient 208, suggest a treatment plan to the patient 208, and/or study the efficacy of an ongoing treatment plan.

Figure 5:
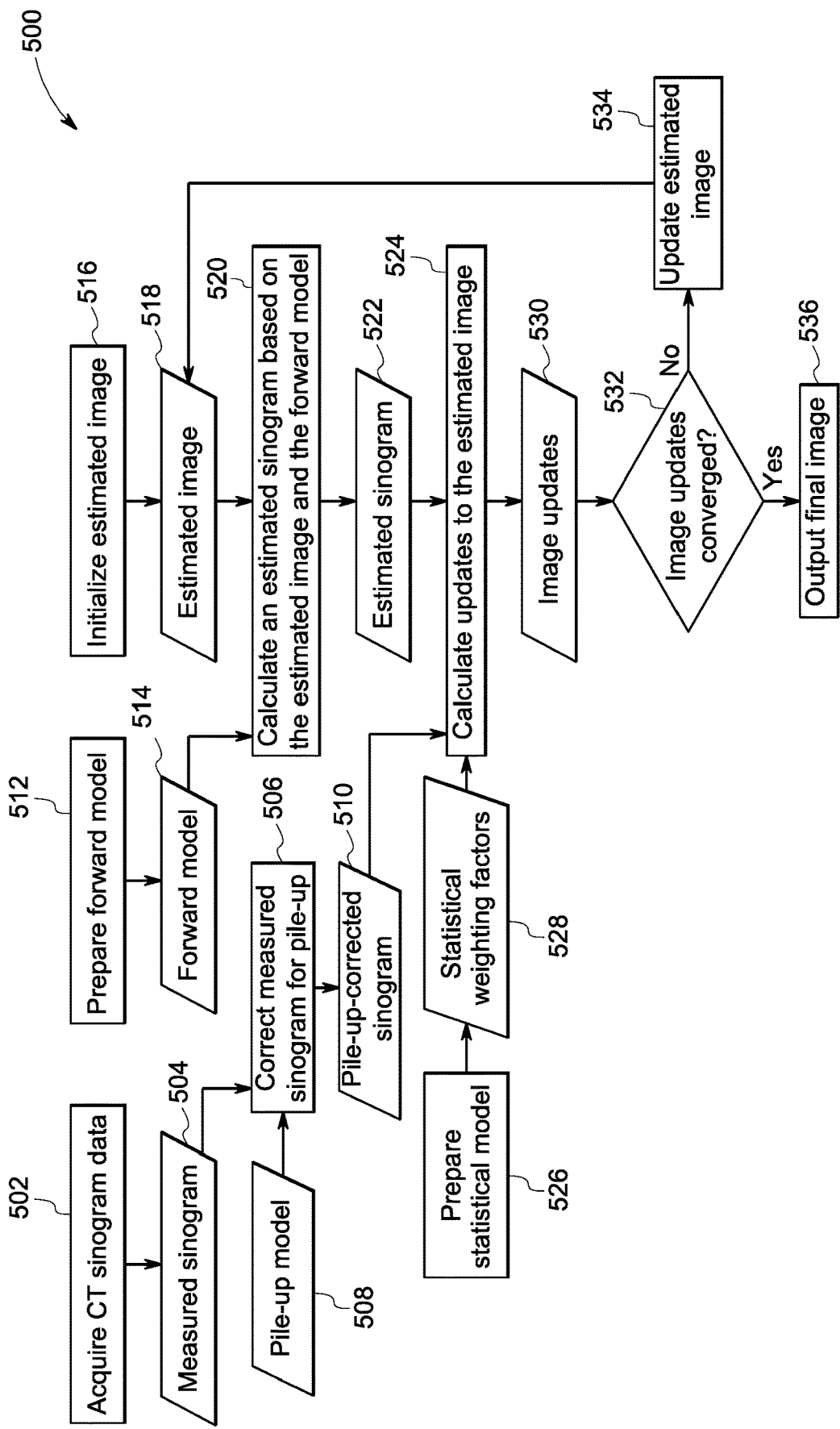
FIG. 5 depicts a flow chart illustrating another exemplary method for imaging, in accordance with aspects of the present specification.

FIG. 5 represents a flowchart 500 of exemplary logic for another method of imaging. In accordance with exemplary aspects of the present specification, another method for enhancing image quality in PCCT systems via use of a model that incorporates unique statistical properties of X-ray pile-up is presented. The method 500 of FIG. 5 is substantially similar to the method 400 depicted in FIG. 4. However, in the method 500, a measured sinogram is corrected for pile-up based on a pile-up model and a pile-up corrected measured sinogram is used to calculate updates to an estimated image. The method 500 is described with reference to the components of FIGS. 1-3. Further, in certain embodiments, the noise correction platform 114 may be employed to perform the steps of the method 500.

The method 500 starts at step 502 where a CT scan of the patient 208 is performed to acquire CT projection data corresponding to one or more anatomical regions of interest in a patient such as the patient 102, 208. The acquired projection images are combined to form a measured sinogram 504.

Additionally, in the method 500 of FIG. 5, at step 506, the measured sinogram 504 is corrected for pile-up. In one embodiment, a pile-up model 508 is used to correct any pile-up effects in the measured sinogram 504 to generate a pile-up-corrected sinogram 510.

Furthermore, at step 512, a forward model 514 is formulated or prepared. As previously noted, the noise correction platform 114 is configured to acquire pile-up characteristics and dead time characteristics of the detector 212 of the imaging system 200 and system characteristics of the imaging system 200. Also, in one embodiment, the forward model 514 is generated by modeling a behavior of the imaging system 200 based on the system characteristics, while in other embodiments, the forward model 514 is generated by modeling a behavior of the imaging system 200 based on system considerations, such as, but not limited to, pile-up characteristics, dead time characteristics, system characteristics, measured system behavior, or combinations thereof.

Moreover, an estimated image 518 may be initialized, as indicated by step 516. In one embodiment, the estimated image 518 may be initialized by setting all pixels to "1." In other embodiments, a filtered back projection image may be used to initialize the estimated image 518. Also, at step 520, an estimated sinogram 522 is generated based on the estimated image 518 and the forward model 514.

As previously noted with reference to FIG. 4, the estimated sinogram 522 is employed to generate a reconstructed image. Accordingly, it is desirable that the estimated sinogram 522 be directly comparable to the pile-up-corrected sinogram 510 to facilitate the generation of a high-quality reconstructed image. Therefore, in certain situations, it may be desirable to determine one or more updates to the estimate image 518.

Accordingly, as indicated by step 524, one or more updates to the estimated image 518 are calculated based a statistical model and the measured pile-up corrected sinogram 510. To that end, in the example of the method 500, the estimated sinogram 522 is compared to the measured pile-up corrected sinogram 510. In particular, a statistically-weighted difference between the estimated sinogram 522 and the measured pile-up corrected sinogram 510 is determined.

Accordingly, at step 526, a statistical model is generated and used to determine the statistically-weighted difference between the estimated sinogram 522 and the measured pile-up corrected sinogram 510. The statistical model includes one or more statistical weighting factors 528, where the statistical weighting factors 528 are employed to determine the statistically-weighted difference between the estimated sinogram 522 and the measured pile-up corrected sinogram 510. As previously noted with reference to FIG. 4, the statistical model is generated based on the statistical behavior of the detector 212 of the imaging system 200. In certain examples, the statistical model is generated based on the pile-up characteristics and the dead time characteristics of the detector with pile-up.

As previously noted with reference to FIG. 4, the unique statistical properties of X-ray pile-up are incorporated into the statistical noise model of an iterative algorithm for statistical image reconstruction or material decomposition for PCCT imaging. In particular, the exemplary statistical noise model of statistical behavior of a detector with pile-up is incorporated into an objective function in an optimization step of the SIR algorithm, thereby performing at least one of optimizing the noise and reducing artifacts in the reconstructed image. The step of determining the update(s) is typically performed as an optimization of an objective function, for example, a weighted least squares cost function or a log-likelihood function. It may be noted that the more closely the estimated sinogram 522 matches the pile-up corrected sinogram 510, the objective function is closer to its optimum.

In certain embodiments, the statistical weighting factors 528 may be included with a set of weighting factors that is used in calculating the objective function. These weights represent different features by which the model and measurements can be compared to each other. By incorporating different factors into the cost function and optimizing the weight factors, the resulting image may be optimized to produce the desired image quality. Incorporating the statistical noise model into the objective function during the optimization step emulates the effect of optimizing noise in the reconstructed image by accounting for the statistical uncertainty in respective measurements.

Additionally, an update to the estimated image 518 is computed based on the statistically-weighted difference between the estimated sinogram 522 and the pile-up-corrected sinogram 510. Subsequent to the processing of step 524 via the statistical model or statistical weighting factors 528, one or more image updates 530 are generated.

Once the image updates 530 are determined, the current estimated image 518 is updated based on the determined update(s) 530 to generate an updated estimated image 518. Prior to updating the estimated image, at step 532, a check is carried out to verify if the determined image update 530 has converged. In one example, convergence of the image update 530 may be determined by comparing the determined image update 530 or functionals thereof with a determined threshold.

At step 532, if it is determined that the image update 530 has not converged, then the estimated image 518 is updated via use of the determined image update 530 to generate an updated estimated image, as indicated by step 534. Also, control is passed to step 520.

Steps 518-534 may be iteratively repeated until the determined image update 530 converges. As previously noted, in a first iteration, the estimated image 518 serves as an input to the iterative process of steps 518-534, and the updated estimated image is generated as an output to the iterative process of steps 518-534. Accordingly, for a subsequent iteration, the updated estimated image serves as an input to the iterative process of steps 518-534.

However, at step 532, if it is determined that the image update 530 has converged, the estimated image may be output as a final reconstructed image, as indicated by step 536. In one example, the final reconstructed image may be visualized on a display such as the display 118 of FIG. 1. The estimated image so generated is representative of a reconstructed image that presents the best match with the pile-up-corrected sinogram 510. This reconstructed image represents an image of enhanced quality where the effects of at least one of noise and image artifacts have been optimized/reduced via use of the statistical noise model. A clinician may use this reconstructed image to provide a diagnosis to the patient 208, suggest a treatment plan to the patient 208, and/or study the efficacy of an ongoing treatment plan.

Figure 6:
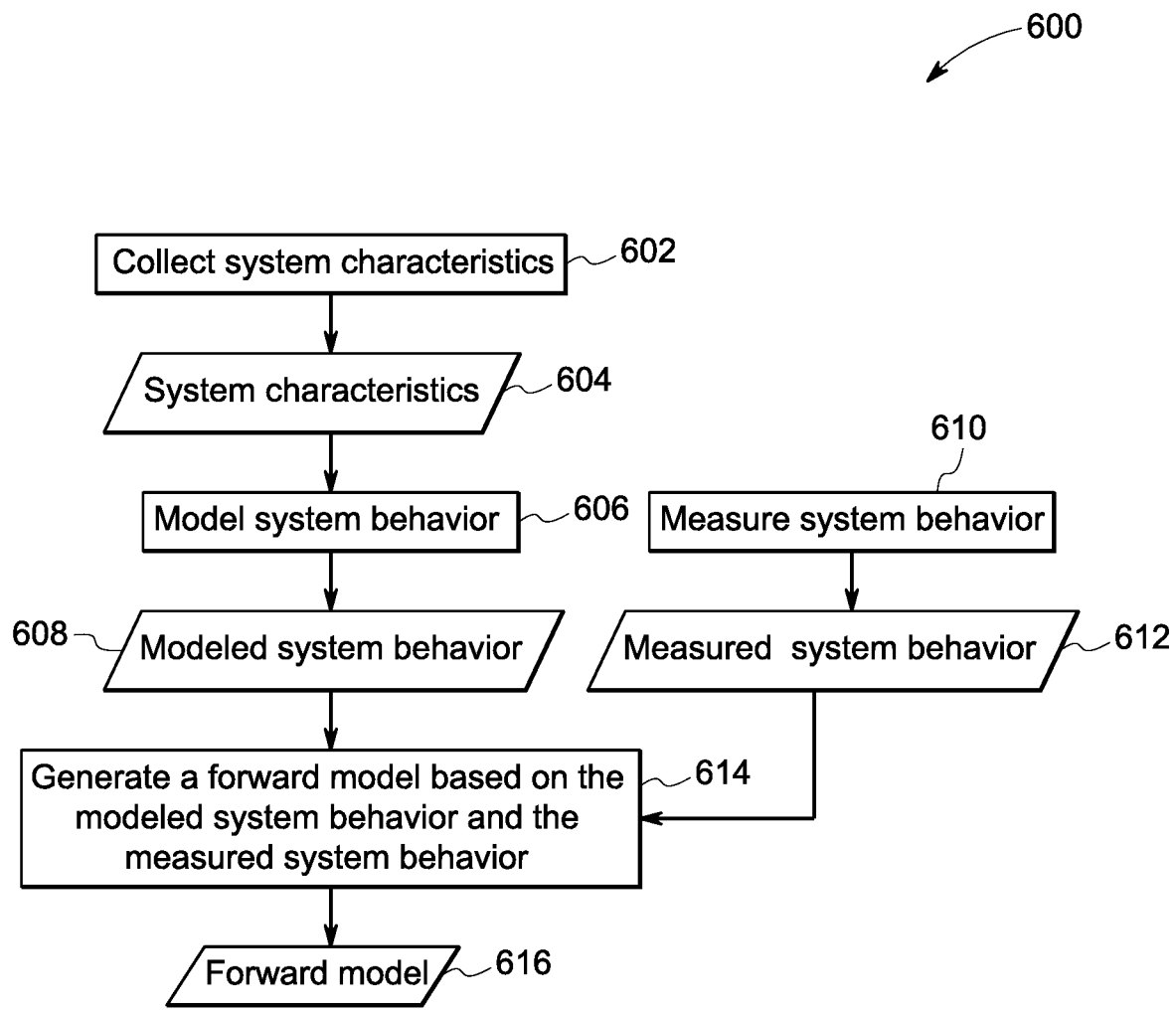
FIG. 6 depicts a flow chart illustrating an exemplary method for formulating a forward model for use in the method of FIG. 4, in accordance with aspects of the present specification.
Figure 7:
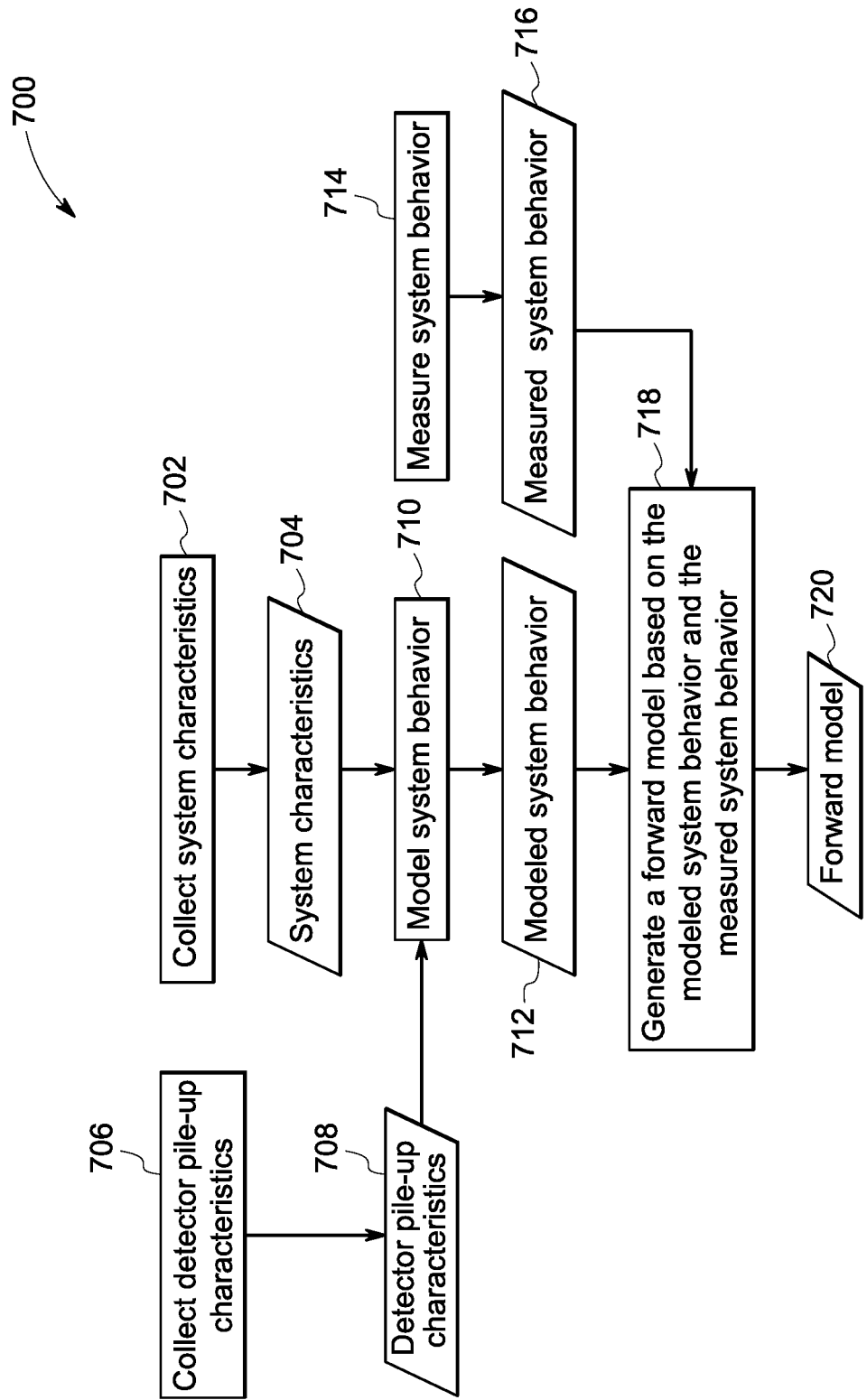
FIG. 7 depicts a flow chart illustrating another exemplary method for formulating a forward model for use in the method of FIG. 5, in accordance with aspects of the present specification.

As noted hereinabove with reference to FIGS. 4-5, a forward model such as the forward models 408, 514 are generated at steps 406 and 512, respectively. FIGS. 6-7 depict two methods of generating a forward model for use in the methods of FIGS. 4-5.

As will be appreciated, processing the acquired image data via an SIR algorithm entails generating reconstructed images such that these reconstructed images result in estimated sinograms that best match a set of measured sinograms corresponding to a CT scan. In one example, it is desirable to generate reconstructed images such that these reconstructed images result in estimated sinograms that are statistically the best match to a set of measured sinograms corresponding to a CT scan based on a statistical model used during the SIR. In particular, during each iteration of the SIR algorithm, the reconstructed image is processed via a forward model to generate an estimated sinogram. The forward model includes known geometry and other characteristics of the imaging system 100. More particularly, the forward model simulates attenuation of X-rays as they pass from an X-ray source, through a patient and impinge upon the detector of the CT imaging system.

FIGS. 6-7 presents methods of generating a forward model for use in the methods of imaging 400, 500 of FIGS. 4-5. In one embodiment, a pile-up correction may be applied to a measured sinogram via use of a pile-up model. In this example, the method of generating the forward model does not include a pile-up model. In certain other embodiments, the pile-up model may be incorporated into the forward model.

Turning now to FIG. 6, a flowchart 600 depicting a method of generating a forward model of step 406 of FIG. 4 is presented. The method 600 is described with reference to the components of FIGS. 1-5. Further, in certain embodiments, the noise correction platform 114 may be employed to perform the steps of the method 600.

The method 600 starts at step 602 where system characteristics 604 corresponding to the imaging system 100 are collected. Some non-limiting examples of the system characteristics 604 include source-to-detector distance, pre-patient filtration, X-ray source tube current and voltage, geometric efficiency, detector materials and dimensions, detector electronics characteristics, X-ray transmission through objects of varying materials and dimensions, and the like.

Further, at step 606, a behavior of the imaging system 100 is modeled based on the system characteristics 604. Reference numeral 608 is generally representative of the modeled system behavior of the imaging system 100. Furthermore, the behavior of the imaging system 100 may be measured, as depicted by step 610, to generate measured system behavior 612. In one example, the behavior of the imaging system 100, such as the X-ray count rate as a function of the system characteristics 604 may be measured by adjusting the system control settings (e.g., tube current and voltage) to representative values, running the imaging system 100 to collect projection data from the imaging system 100, and quantifying the relationships between the system control settings and the projection data. Various objects may be used in the imaging system 100 to play the role of the patient 102, so called imaging phantoms. These imaging phantoms may be specially designed to facilitate characterizing the system behavior. Similarly, the behavior of the imaging system 100 may also be modeled using a variety of analytical and numerical methods to predict the response of the imaging system 100 with different settings and object characteristics. For example, the X-ray transmission through a patient 102 of a given thickness and material composition may be modeled using the X-ray energy spectrum and well-known values of X-ray attenuation coefficients for the materials. It may also be noted that the X-ray spectrum itself may be a result of a model or may be measured using suitable instruments from an output of a real X-ray source such as the X-ray source 202. Similar methods may be used to model the absorption of X-rays in the detector 212, the generation of signals from the deposited energy, the conversion of those signals into digital data, and subsequent processing of the digital data.

Subsequently, at step 614, a forward model 616 may be generated based on at least one of the modeled system behavior 608 and the measured system behavior 612. In some embodiments, the forward model 616 includes a set of computer instructions for calculating a predicted output of the imaging system 100 based on an input set of system characteristics and object properties. More specifically, in one embodiment, the output is the predicted number of X-rays detected in each pixel of the detector 212, and falling into ranges of energy or pulse height defined by the energy bins of the detector electronics, in response to inputs of particular X-ray source settings, system geometry, as well as patient materials and dimensions. The modeled system behavior 608 and the measured system behavior 612 may be combined to predict the outputs based on the inputs. The forward model 616 so generated may be employed in situations where pile-up is not used as an input to the forward model. For example, the forward model 616 may be used as the forward model 408 in the method 400 of FIG. 4.

FIG. 7 is a flowchart 700 depicting a method of generating a forward model such as the forward model 514 of step 512 of FIG. 5. Also, the method 700 is described with reference to the components of FIGS. 1-6. Moreover, in one embodiment, the noise correction platform 114 may be employed to perform the steps of the method 700.

The method 700 starts at step 702 where system characteristics 704 corresponding to the imaging system 100 are collected. In one example, the system characteristics 704 include source-to-detector distance, pre-patient filtration, X-ray source tube current and voltage, geometric efficiency, detector materials and dimensions, detector electronics characteristics, X-ray transmission through objects of varying materials and dimensions, and the like.

Moreover, at step 706, detector characteristics 708 are collected. It may be noted that in certain embodiments, the detector characteristics 708 may be collected as a part of the system characteristics 704. The detector characteristics 708 may include characteristics that influence the pile-up behavior of the detector 212, such as geometric efficiency, pixel size, material composition and corresponding energy absorption, charge generation and transport, charge pulse shape, electronics bandwidth, electronics triggering, dead time characteristics, and the like.

Further, at step 710, a behavior of the imaging system 100 is modeled based on the system characteristics 704 and the detector characteristics 708. Reference numeral 712 is generally representative of the modeled system behavior of the imaging system 100. Additionally, the behavior of the imaging system 100 may be measured, as depicted by step 714 to generate measured system behavior 716. In one example, the behavior of the imaging system 100, such as the X-ray count rate as a function of the system characteristics 704 may be measured by adjusting the system control settings (e.g., tube current and voltage) to representative values, running the imaging system 100 to collect projection data from the imaging system 100, and quantifying the relationships between the system control settings and the projection data. Various objects may be used in the imaging system 100 to play the role of the patient 102, so called imaging phantoms. These imaging phantoms may be specially designed to facilitate characterizing the system behavior. Similarly, the behavior of the imaging system 100 may also be modeled using a variety of analytical and numerical methods to predict the response of the imaging system 100 with different settings and object characteristics. For example, the X-ray transmission through a patient 102 of a given thickness and material composition may be modeled using an X-ray energy spectrum and well-known values of X-ray attenuation coefficients for the materials. It may also be noted that the X-ray spectrum itself may be a result of a model or may be measured using suitable instruments from an output of a real X-ray source such as the X-ray source 202. Similar methods may be used to model the absorption of X-rays in the detector 212, the generation of signals from the deposited energy, the conversion of those signals into digital data, and subsequent processing of the digital data.

Subsequently, at step 718, a forward model 720 is generated based on at least one of the modeled system behavior 712 and the measured system behavior 716. In some embodiments, the forward model 720 includes a set of computer instructions for calculating a predicted output of the imaging system 100 based on an input set of system characteristics and object properties. More specifically, in one embodiment, the output is the predicted number of X-rays detected in each pixel of the detector 212, and falling into ranges of energy or pulse height defined by the energy bins of the detector electronics, in response to inputs of particular X-ray source settings, system geometry, as well as patient materials and dimensions. The modeled system behavior 712 and the measured system behavior 716 may be combined to predict the outputs based on the inputs. The forward model 720 so generated may be employed in situations where pile-up is used as an input to the forward model. For example, the forward model 720 may be used as the forward model 514 in the method 500 of FIG. 5.

Figure 8:
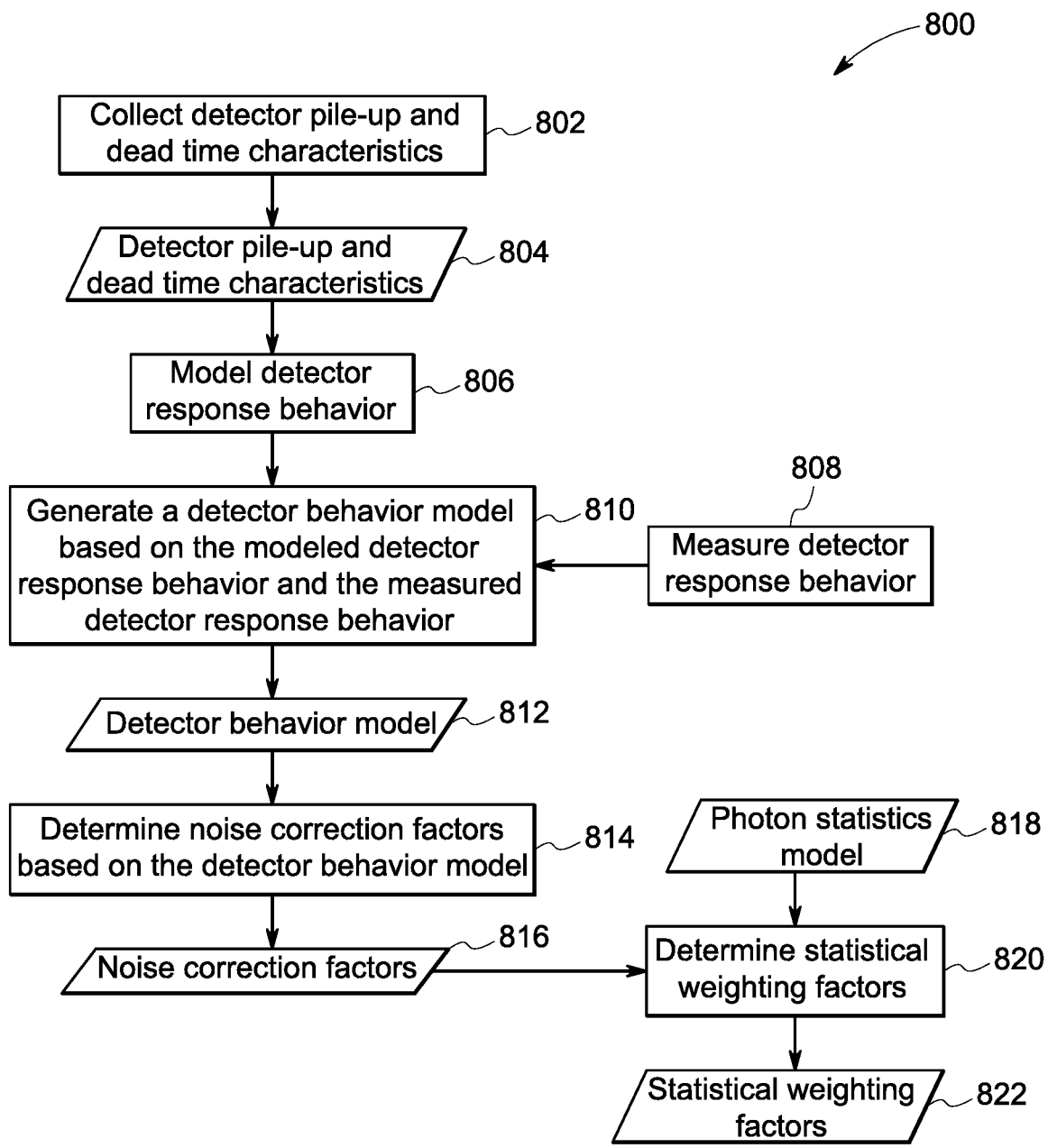
FIG. 8 depicts a flow chart illustrating an exemplary method for formulating a statistical model for use in the methods of FIGS. 4-5, in accordance with aspects of the present specification.
Figure 9:
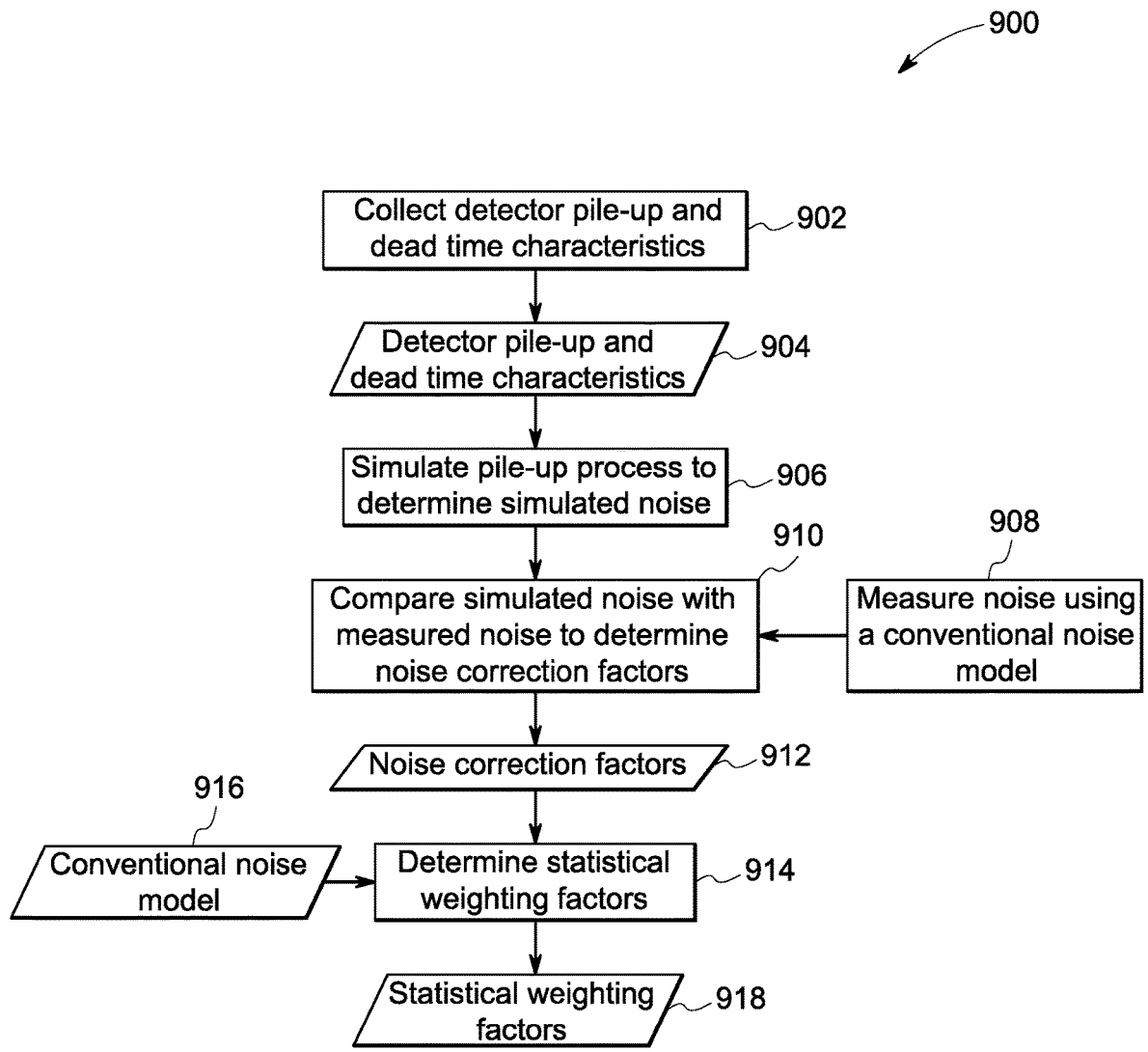
FIG. 9 depicts a flow chart illustrating another exemplary method for formulating a statistical model for use in the methods of FIG. 4-5, in accordance with aspects of the present specification.
Figure 10:
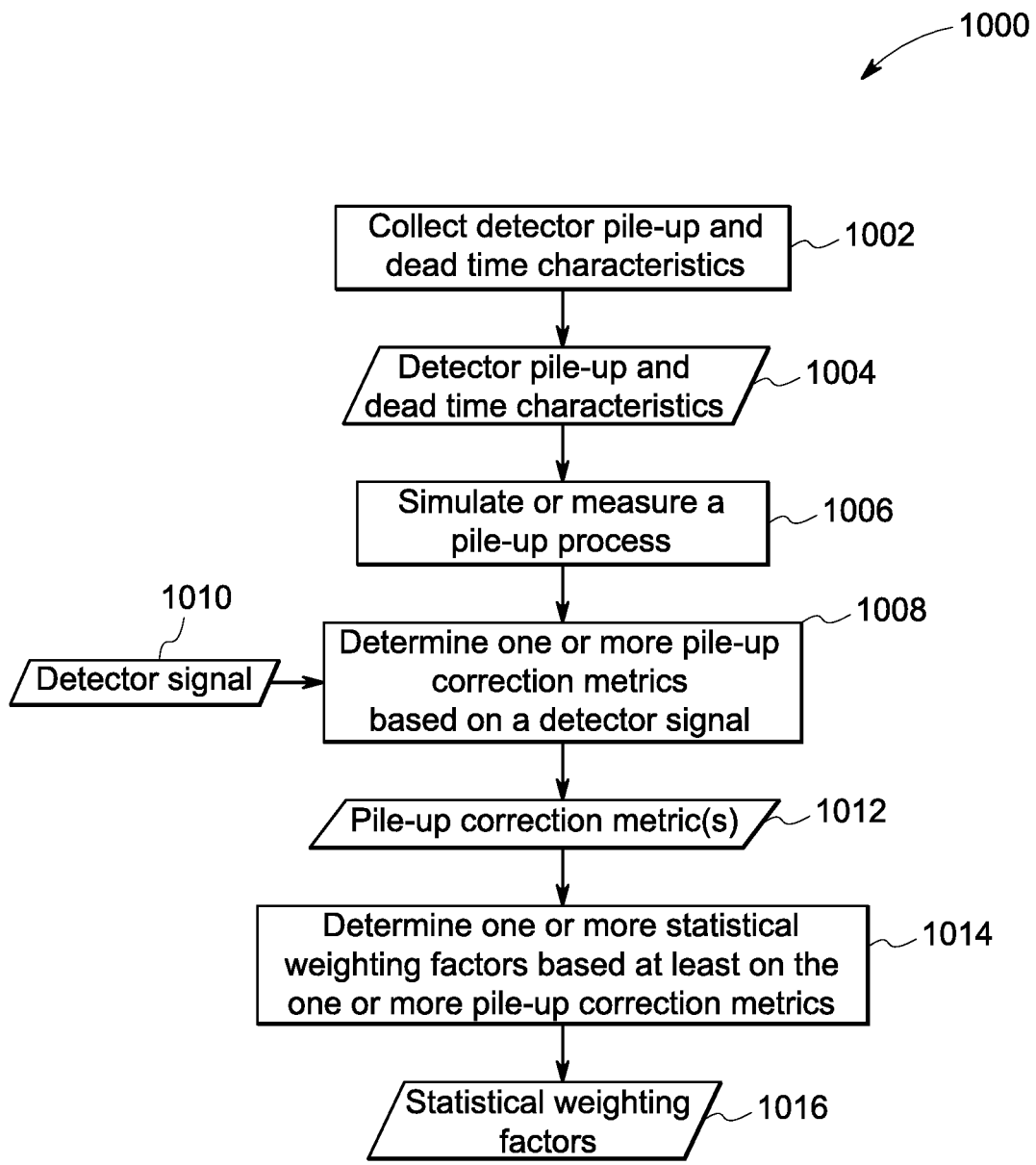
FIG. 10 depicts a flow chart illustrating yet another exemplary method for formulating a statistical model for use in the methods of FIGS. 4-5, in accordance with aspects of the present specification.

As previously described with reference to FIGS. 4-5, a statistical model is employed to determine a statistically-weighted difference between an estimated sinogram and a measured sinogram, or a pile-up-corrected sinogram, where the statistically-weighted difference so determined is employed to determine an update to an estimated image. Also, the statistical model includes one or more statistical weighting factors. In certain examples, the statistical model is generated based on the pile-up characteristics and the dead time characteristics of the detector with pile-up. In an alternative embodiment, the statistical weighting factors may be replaced by weights that relate to the fidelity of the data. For example, the weights may be indicative of the amount of pile-up in the measurements—lower weights for higher amounts of pile-up and higher weights for lower amounts of pile-up. FIGS. 8-10 present various methods of generating the statistical model. In particular, the formulation of the statistical model of steps 420 (see FIG. 4) and 526 (see FIG. 5) are described with reference to FIGS. 8-10.

Turning now to FIG. 8, a flowchart 800 of one method of formulating a statistical model is presented. The method 800 is described with reference to the components of FIGS. 1-7. Moreover, in one embodiment, the noise correction platform 114 may be employed to perform the steps of the method 800.

The method starts at step 802 where pile-up characteristics and dead time characteristics of the detector 212 of the imaging system 200 are collected. Reference numeral 804 is generally representative of the pile-up characteristics and dead time characteristics of the detector 212. As previously noted, the pile-up characteristics and dead time characteristics 804 of the detector 212 may include a sensor output pulse shape, electronics pulse response characteristics, electronics triggering logic and timing, electronics trigger arming (dead time) logic and timing, and the like.

Further, a response behavior of the detector 212 is modeled, as depicted by step 806. Also, at step 808, a response behavior of the detector 212 is measured. In one example, the behavior of the imaging system 100, such as the X-ray count rate as a function of the system characteristics may be measured by adjusting the system control settings (e.g., tube current and voltage) to representative values, running the imaging system 100 to collect projection data from the imaging system 100, and quantifying the relationships between the system control settings and the projection data. Various objects may be used in the imaging system 100 to play the role of the patient 102, so called imaging phantoms. These imaging phantoms may be specially designed to facilitate characterizing the system behavior. Similarly, the behavior of the imaging system 100 may also be modeled using a variety of analytical and numerical methods to predict the response of the imaging system 100 with different settings and object characteristics. For example, the X-ray transmission through a patient 102 of a given thickness and material composition may be modeled using the X-ray energy spectrum and well-known values of X-ray attenuation coefficients for the materials. It may also be noted that the X-ray spectrum itself may be a result of a model or may be measured using suitable instruments from an output of a real X-ray source such as the X-ray source 202. Similar methods may be used to model the absorption of X-rays in the detector 212, the generation of signals from the deposited energy, the conversion of those signals into digital data, and subsequent processing of the digital data.

Currently, noise models for use in iterative processes for noise as a function of measured counts are available. In one example of a currently available noise model, the pile-up behavior of the detector may be characterized through a calibration procedure, where the detector is exposed to representative flux conditions covering the entire operating range, for various combinations of material compositions within the X-ray beam.

Further, at each condition, the mean and variance in counts may be tabulated and represented in a functional form as:

$$m(n;p) \tag{1}$$

where m is the measured number of counts and n is the true incident number of counts for a particular condition specified by parameters p such as view time, X-ray source kVp and mA, collimation, and the like.

Moreover, to determine the true count value and expected noise for a pixel with m measured counts, a reverse lookup table may be generated by inverting the function of equation (1) to obtain:

$$\hat{n}(m;p) \tag{2}$$

where $\hat{n}$ is the estimate of the true count value.

This reverse lookup table may be implemented by parameterizing the data with curve fitting, by linear or non-linear interpolation, or other methods.

In another example, a calibration experiment may be performed to obtain a set of calibration data consisting of a nominal count n_k, a measured count m_k, and a variance v_k for each energy bin k and for each detector channel c. Further, this calibration data for a given detector channel may be used to convert an actual set of energy bin measurements {m_k} into a set of corrected measurements {c_k} and a set of variances {v_k}, via use of a lookup table, an analytic expression such as a polynomial, or a neural network.

It may be noted that although the true count value n and its variance $\sigma^2$ may be estimated from the measured count value m based on the conversion methods noted hereinabove, such estimations in practical applications can only be made from a single noisy measurement. Consequently, the estimated count value n and the estimated variance $\hat{\sigma}^2$ are also subject to statistical noise. The noise in the estimated variance $\hat{\sigma}^2$, which is usually highly correlated with the statistical noise in the estimated count value $\hat{n}$, may lead to a systematical bias in iteratively reconstructed images. This issue exists for all CT systems and may become more noticeable for PCCT systems because the number of X-ray photons detected in each individual energy bin will be lower than that in a conventional energy-integrating system operating at a similar flux level.

In accordance with aspects of the present specification, a detector behavior model 812 is generated at step 810, where the detector behavior model 812 is configured to circumvent the shortcomings of the presently available techniques. The detector behavior model 812 is generated based on at least one of the modeled detector response behavior, the measured detector response behavior, the pile-up characteristics of the detector, the dead time characteristics of the detector, or combinations thereof. It may be noted that the detector behavior model 812 aids in improving the precision of the estimated variance $\hat{\sigma}^2$.

Moreover, in accordance with further aspects of the present specification, a model of the statistical behavior of a detector with pile-up (the detector behavior model 812) may be generated and incorporated into an objective function in an optimization step of an iterative algorithm such as the SIR process. Incorporating the detector behavior model of the detector with pile-up into the objective function in the optimization step aids in at least one of optimizing noise and reducing artifacts in a reconstructed image by accounting for statistical uncertainty in the respective measurements.

As will be appreciated, traditionally, the variance $\sigma^2$ is estimated from a single measurement m. In accordance with aspects of the present specification, in one embodiment, the variance $\sigma^2$ is estimated from multiple neighboring detector channels as follows:

$$\hat{\sigma}_i^2 = f(\ldots, m_{i-1}, m_i, m_{i+1} \ldots; p) \qquad (3)$$

where i denotes a detector cell index and $f(\cdot)$ is an estimator, and parameters p are similar to those listed in equation (1).

Further, the estimator $f(\cdot)$ may apply denoising filters (such as a box car filter, a Gaussian filter, or other more advanced filters) or a neural network to the measured data $m_i$'s before estimating the variance $\hat{\sigma}^2$. Consequently, the noise in estimated variance $\hat{\sigma}^2$ may be reduced and the correlation with the noise in the estimated count value $\hat{n}$ may also be reduced. The estimator $f(\cdot)$ may be spatially adaptive and configured to apply stronger denoising strength in relatively uniform sinogram regions.

In accordance with another embodiment of the present specification, instead of estimating the variance $\sigma^2$ from a single measurement m, the variance $\sigma^2$ may be estimated from multiple energy bins for a given pixel as follows:

$$\hat{\sigma}_k^2 = g(m_1, \ldots, m_k, \ldots, m_K; p) \qquad (4)$$

where k denotes an energy bin index and $g(\cdot)$ is an estimator, and parameters p are similar to those listed in equation (1).

Moreover, the estimator $g(\cdot)$ may reduce the noise in the measurements $m_k$ by fitting a multi-energy vector to lower-dimensional principal components that incorporate prior knowledge about materials present within the CT system and associated basis material physics. The energy spectral domain method may also be combined with the spatial domain method.

Conventionally, the variance $\sigma^2$ is estimated from the measured sinogram. In accordance with yet another embodiment of the present specification, the variance $\sigma^2$ may be estimated from the estimated sinogram that is generated by an iterative reconstruction process as follows:

$$\sigma^2 = h(\hat{m}^{(n)}) \qquad (5)$$

where $\hat{m}^{(n)}$ denotes the estimated sinogram generated by the iterative reconstruction process at the $n^{th}$ iteration.

Accordingly, the detector behavior model 812 facilitates estimation of the estimated variance with greater precision. Such an estimation may be repeated iteratively, along with the estimation of the reconstructed image. Similarly, the statistical weighting factors may also be updated based on the newly estimated variance 82 to improve the precision of the statistical weighting factors and to reduce bias in the final reconstructed image.

It may be noted that a set of weighting factors may be used in defining the objective function of the SIR algorithm. These weights or weighting factors represent the metric by which a model and measurements may be compared to each other. By incorporating the weighting factors into the cost function and optimizing the cost function, the resulting reconstructed image may provide more desirable image quality in terms of reduction of noise and/or image artifacts.

One example of a factor incorporated into the cost function is a weighting term based on the noise variance of the measurements. This factor aids in reducing the noise or noise-induced artifacts in the reconstructed images by taking into account the level of uncertainty in the respective measurements. Moreover, use of the detector behavior model 812 aids in further reducing the noise in the reconstructed images.

As will be appreciated, in PCCT imaging systems, individual X-ray photons are recorded when the photons interact with the detector. Disadvantageously, PCCT imaging systems suffer from imperfect counting of X-rays that arrive too close together in time, especially for measurements at high X-ray flux, and/or regions of a sinogram with little attenuation through the patient and the X-ray source pre-patient filter (bowtie).

In addition to its impact on the number of counts recorded, pile-up also impacts the noise in a CT projection. Noise in a CT projection data typically increases with the X-ray flux, following approximately a Poisson distribution, meaning that the variance in the number of X-rays ($\sigma^2$) is equal to the expected number of X-rays, or more generally, the variance on the measurements is proportional to the expected value of the respective measurements. When pile-up occurs, both the number of counts and the variation in counts are reduced. Additionally, when pile-up occurs, the noise no longer follows a Poisson distribution.

In one example representative of extreme pile-up, for a non-paralyzable detector all the pixels tend to become saturated and produce an identical number of counts. In this case the noise variance will be exactly zero. Also, in this example, the detector signal fails to carry any meaningful intensity information either. More generally, as the X-ray flux increases in a non-paralyzable detector with pile-up, the noise at first increases, reaches a maximum and then decreases gradually to zero.

Accordingly, at step 814, one or more noise correction factors 816 are determined based on the detector behavior model 812. The noise correction factors 816 are representative of a factor that is incorporated into the cost function as a weighting term based on the noise variance of the measurements. In particular, the noise correction factors 816 are configured to aid in reducing the noise in the reconstructed images by taking into account the level of uncertainty in the respective measurements. Specifically, the noise is multiplied by a noise correction factor 816 to provide a corrected estimate of the noise. It may be noted that the noise correction factors 816 may have a different value for different inputs, different pixels, different energies, and different count rates. In one embodiment, the noise correction factor 816 is a function of inputs such as a count rate and has multiple parameters such as characteristics of the imaging system 100 like the electronics dead time, which determine the amount of pile-up that occurs at a given count rate.

Figure 13:
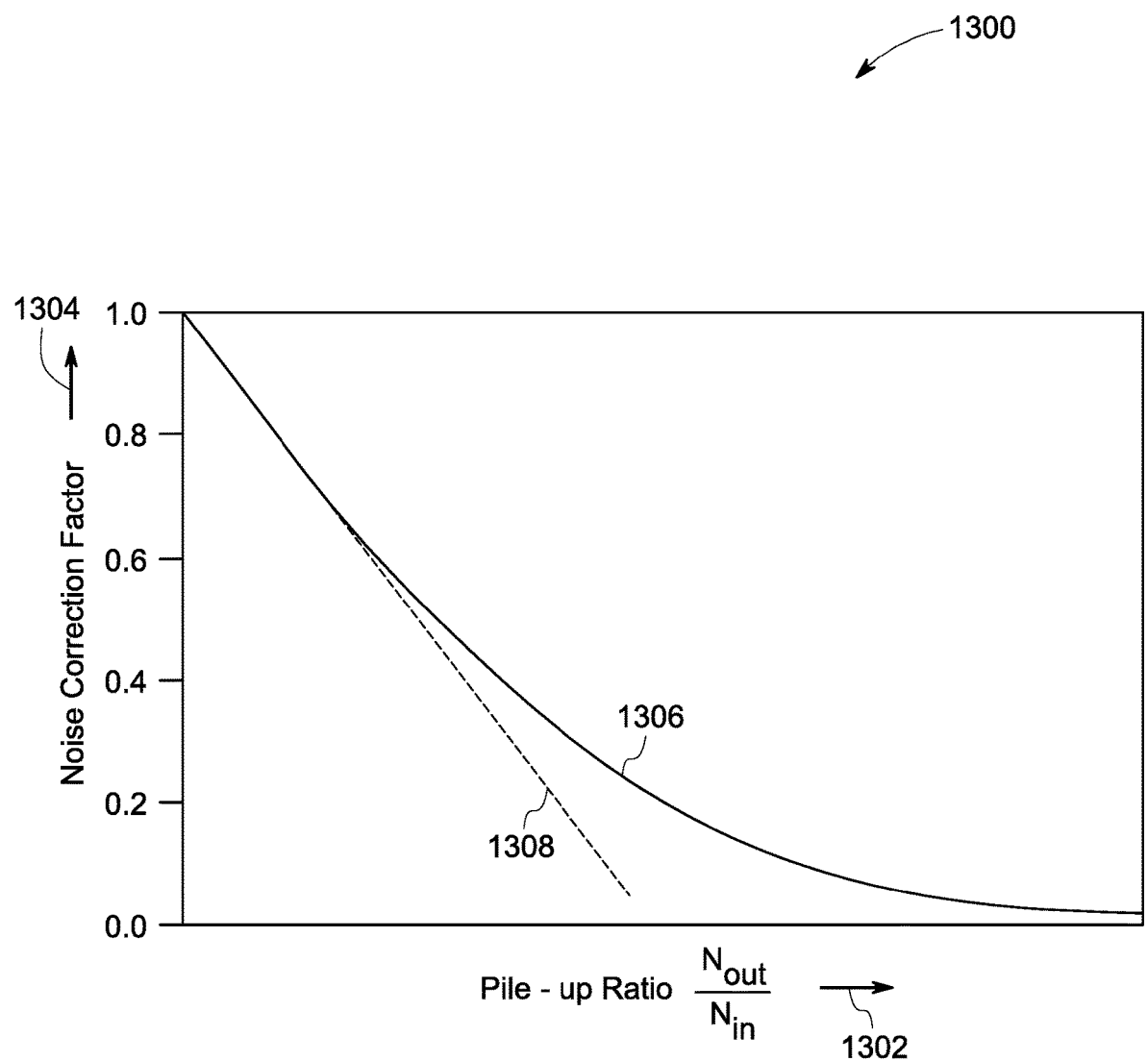
FIG. 13 depicts a graphical representation of one embodiment of a noise pile-up correction factor, in accordance with aspects of the present specification.

A graphical representation of the general behavior of the noise correction factor 816 as a function of pile-up ratio is depicted in FIG. 13. In certain embodiments, the noise correction factor 816 has a value of unity for the lowest count rate. Further, the noise correction factor 816 approaches a zero value in an approximately asymptotical fashion at high count rates.

Also, one or more statistical weighting factors 822 are determined, as indicated by step 820. In particular, the statistical weighting factors 822 are determined based on the noise correction factors 816 and a photon statistics model 818. Typically, the photon arrival statistics are modeled as a Binomial, Poisson, or Gaussian random process. These statistical weighting factors 822 are used to compute an update to the estimated image, thereby accounting for the statistical variability of the measurements. One example of determining the statistical weighting factors will be described in greater detail with reference to step 914 of FIG. 9.

FIG. 9 presents a flowchart 900 depicting another method for formulating a statistical model. The method 900 is described with reference to the components of FIGS. 1-8. Also, in certain embodiments, the noise correction platform 114 may be employed to perform the method 900.

The method 900 starts at step 902 where pile-up characteristics and dead time characteristics of the detector 212 of the imaging system 200 are collected. Reference numeral 904 is generally representative of the pile-up characteristics and dead time characteristics of the detector 212. As previously noted, the pile-up characteristics and dead time characteristics 904 of the detector 212 may include a sensor output pulse shape, electronics pulse response characteristics, electronics triggering logic and timing, electronics trigger arming (dead time) logic and timing, and the like.

Further, at step 906, the pile-up characteristics and the dead time characteristics 904 of the detector 212 are employed to determine simulated noise in the measured counts in the pixels of the detector. The simulated noise serves as a ground truth of the noise. In particular, a simulated noise model may be determined based on the pile-up characteristics and dead time characteristics 904. Moreover, noise corresponding to one or more configurations of the imaging system 100 may be simulated based on the simulated noise model. By way of a non-limiting example, the noise behavior of the imaging system 100 may be simulated for different parameters such as tube current, kVp, patient size, and the like that are encountered in a clinical environment.

Moreover, as indicated by step 908, noise in the measured counts may be measured via use of a conventional noise model. Some examples of the conventional noise model include a Poisson model or a Gaussian model. It may be noted that the conventional noise model does not include pile-up characteristics and/or dead time characteristics.

Subsequently, at step 910, the simulated noise is compared with the measured noise to determine one or more noise correction factors 912. In one example, a lookup table may be used to determine the noise correction factors 912. Also, at step 914, one or more statistical weighting factors 918 are determined based on the noise correction factors 912 and a conventional noise model 916.

In accordance with aspects of the present specification, the noise correction factor 912 is used to generate a "corrected" value of the noise. Accordingly, the noise correction factor 912 may be used to correct the measured noise to determine a corrected value of the noise. By way of example, Correct noise=(conventional model of the noise)* (noise correction factor)         (6)

As previously noted, the noise correction factor 912 is a different number for different inputs, different pixels, different energies, and different count rates. More particularly, the noise correction factor 912 is a function of the inputs such as a count rate and has multiple parameters such as characteristics of the imaging system 100 such as the electronics dead time, which aid in determining how much pile-up happens at a given count rate.

Advantageously, the noise correction factors 912 are a more compact representation of the accurate noise model. Moreover, since the currently available iterative reconstruction methods already use a conventional noise model, corrections to the conventional noise model may be added with very minimal changes to produce a more accurate result.

For photon counting CT detectors, when the X-ray photon flux arriving at the detector is high, the signal from the detector may be distorted due to the pile-up of the detector signal. Conventionally, physical model based correction algorithms have been applied to correct the distorted signals. However, the physical model typically has many assumptions and may result in residual artifacts, especially when applied to a complicated system. Model-based iterative reconstruction (MBIR) techniques have also been employed to generate reconstructed images.

In one example, the statistical weighting factors 918 are used in a MBIR algorithm to down-weight projection rays that suffer from the pile-up effect. Typically, in MBIR, statistical weighting factors that may be interpreted as the fidelity of the signal are applied for each projection ray. In accordance with aspects of the present specification, pixels that contain a strong pile-up signal are intentionally down-weighted in order to reduce the corresponding impact on the final reconstructed images.

The absorbed X-ray intensity follows a Poisson distribution as indicated by equation (7):

$$\lambda_i \sim \text{Poisson}(I_i e^{-y_i}) \quad (7)$$

where $\lambda_i$ is the number of absorbed X-rays in a projection ray (or pixel) i, $I_i$ is the intensity of incident X-rays, and $y_i$ is the X-ray projection value (integral of the attenuation coefficient-length product) in projection ray (or pixel) i.

Further, the reconstruction problem may be represented as maximizing the penalized log likelihood function:

$$x = \underset{x}{\mathrm{argmin}}\left\{-\frac{1}{2}(y - Ax)^T W(y - Ax) + U(x)\right\} \quad (8)$$

where W represents the statistical weighting factors, which are proportional to the detector counts if Poisson noise is assumed, y is the projection data, A is the system matrix, x is estimated image data, and U is an image regularization function.

When the signal is corrupted by pile-up, a physical model based pile-up correction may be used to first correct the pile-up signal. Some examples of the physical model based pile-up correction are presented in equations (9) and (10).

$$y \xrightarrow{pile-up\ correction} y_{corr} \quad (9)$$

$$W \xrightarrow{pile-up\ correction} W_{corr} \quad (10)$$

Subsequently, the problem may be formulated as:

$$x = \underset{x}{\mathrm{argmin}}\left\{-\frac{1}{2}(y_{corr} - Ax)^T W(y_{corr} - Ax) + U(x)\right\} \quad (11)$$

Additionally, a modulation function may be applied on the weights to further reduce the contribution from the corrupted projection rays. Accordingly, the pile-up residuals may be reduced. Some examples of the modulation function are presented in equations (12) and (13).

$$y_{rescale} = f(y_{corr}) \quad (12)$$

$$W_{rescale} = f(W_{corr}) \quad (13)$$

Moreover, in accordance with further aspects of the present specification, the statistical weighting factors may be adaptively adjusted to suit any measurement. As will be appreciated, an increase in the photon counts results in an increase in the severity of the effect of pile-up. In accordance with aspects of the present specification, the statistical weighting factors for these projection rays may be reduced to decrease the weighting for these rays. In particular, a scaling function may be determined based on the detected signal level. Further, this scaling function may be used to adaptively adjust the statistical weighting factors based on the measurement to suppress the pile-up artifacts in the reconstructed images.

In one non-limiting example, the scaling functions of equations (14) and (15) may be used. Although equations (14) and (15) present the threshold as a constant value, it may be noted that the threshold may be determined based on the dead time and may be optimized accordingly.

$$\text{For a threshold} \leq 5000; \text{weights} = \text{weights} \times e^{1 - \frac{weights}{thresh}} \quad (14)$$

$$\text{For a threshold} > 5000; \text{weights} = \sqrt[3]{\text{weights}} \quad (15)$$

However, other scaling functions may also be used. Moreover, in extreme cases, the weights of the pile-up corrupted projections rays may be totally abandoned. Also, the statistical weighting factors for the projection rays that are not contaminated by pile-up may be intentionally boosted to further suppress the artifacts. Furthermore, it may be noted that the pile-up behavior for different detector architectures may be different. Accordingly, the threshold may be adjusted for different imaging systems.

In addition, in certain embodiments, a transition point may be determined to facilitate further adjustment of the statistical weighting factors for the projection rays. Further, the scaling functions may be differently designed above and below the determined transition point. In certain embodiments, the statistical weighting factors could be replaced by weights that relate to the fidelity of the data. For example, the weights may be indicative of the amount of pile-up in the measurements—lower weights for higher amounts of pile-up and higher weights for lower amounts of pile-up.

Referring now to FIG. 10, a flowchart 1000 depicting yet another method for formulating a statistical model is presented. The method 1000 is described with reference to the components of FIGS. 1-9. Also, in certain embodiments, the noise correction platform 114 may be employed to perform the method 1000.

The method starts at step 1002 where pile-up characteristics and dead time characteristics of the detector 212 of the imaging system 200 are collected. Reference numeral 1004 is generally representative of the pile-up characteristics and dead time characteristics of the detector 212. As previously noted, the pile-up characteristics and dead time characteristics of the detector 212 may include a sensor output pulse shape, electronics pulse response characteristics, electronics triggering logic and timing, electronics trigger arming (dead time) logic and timing, and the like.

Moreover, at step 1006, the pile-up characteristics and the dead time characteristics of the detector 212 are employed to simulate or measure a pile-up process of the detector 212. In one example, pile-up may be simulated by simulating the generation of charge by an X-ray absorption event and transport of generated charge to the collection electrodes. Further, the response of readout electronics may be used to determine how the imaging system 100 will record the response when multiple X-rays arrive close together in time. This process may be carried out for different assumed count rates. The pile-up process of an actual system may be measured by operating the system at increasing levels of X-ray flux and recording or characterizing the output.

Furthermore, one or more pile-up correction metrics 1012 are determined at step 1008. In particular, the pile-up correction metrics 1012 are determined based on a detector signal 1010. Some non-limiting examples of the one or more pile-up correction metrics 1012 include a pile-up ratio, a signal corrected for the pile-up, a deficiency signal corresponding to the pile-up, or combinations thereof. Also, in one example, a lookup table may be used to determine the pile-up correction metrics 1012 based on the detector signal 1010. Subsequently, at step 1014, one or more statistical weighting factors 1016 are determined based at least on the one or more pile-up correction metrics 1014.

In accordance with aspects of the present specification, in addition to the other methods of determining a statistical noise model described with reference to FIGS. 8-10, a statistical noise model may also be determined as a function of measured counts. In particular, the statistical noise model may be determined by deriving a parametric statistical model based on the physics of pile-up. In the case of non-paralyzable detectors, there exists a unique mapping that relates the mean number of counts to the noise level. This mapping may be implemented as a lookup table that provides a relationship between the measured counts and corresponding noise levels. Model parameters for a pixel may then be determined by performing a parametric fit of data from a calibration measurement to the pile-up model.

Moreover, it is desirable that this parametric model accurately describes the actual behavior of the detector of the PCCT imaging system. A simple model of pile-up, the commonly used ideal non-paralyzable detector model, is based on the assumption that photon interactions are converted to pulses in the detector electronics that have zero extent in time. However, this approach is too simplistic to accurately predict the behavior of real photon counting detectors for both low and high count rates.

In accordance with aspects of the present specification, a more accurate model may be derived by assuming that pulses have a finite duration. In this example, the mean and the variance $\sigma^2$ of measured counts are given by:

$$\mu = \frac{\lambda t}{e^{-\lambda \tau_s} + \lambda \tau} \quad (16)$$

$$\sigma^2 = \frac{\lambda t e^{-\lambda \tau_s}(2 - e^{-\lambda \tau_s})}{(e^{-\lambda \tau_s} + \lambda \tau)^3} \quad (17)$$

where λ denotes the true count rate, t denotes the measurement time, τ denotes the dead time of the counter, and $\tau_s$ denotes a fraction of the dead time τ during which a new event may cause a consecutive dead time to be triggered.

Figure 11:
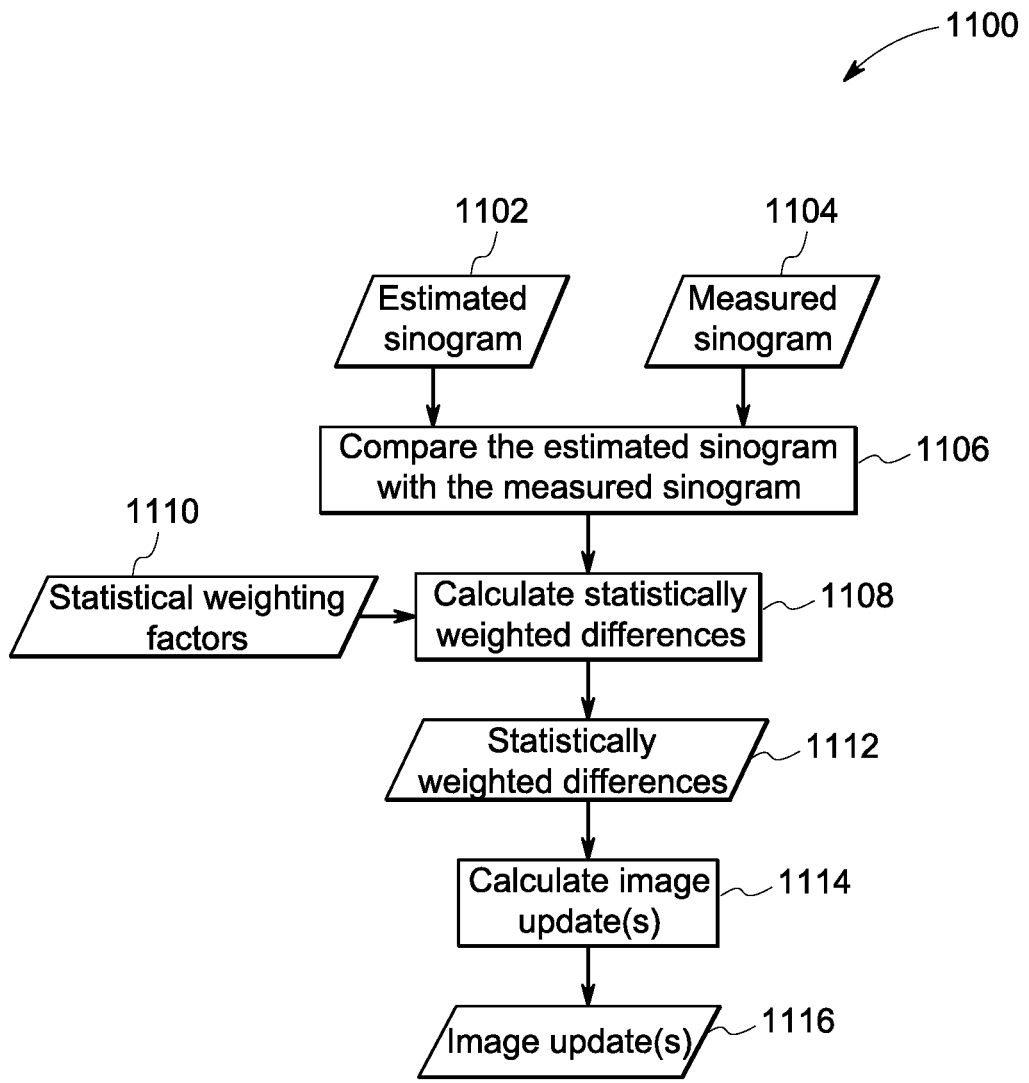
FIG. 11 depicts a flow chart illustrating an exemplary method for determining updates to an estimated image for use in the methods of FIGS. 4-5, in accordance with aspects of the present specification.

As previously described with reference to FIGS. 4-5, an update to the estimated image is calculated/determined based on a statistical model and an estimated sinogram. FIG. 11 presents a method of determining/calculating an update to the estimated image based on the statistical model and the estimated sinogram. In particular, determining the update to the estimated image based on the statistical model of steps 418 (see FIG. 4) and 524 (see FIG. 5) are described with reference to FIG. 11.

FIG. 11 is a flowchart 1100 depicting a method for calculating one or more updates to an estimated image. The method 1100 is described with reference to the components of FIGS. 1-10. Also, in certain embodiments, the noise correction platform 114 may be employed to perform the method 1100.

As will be appreciated, during the SIR process, an estimated sinogram is compared to a measured sinogram. Further, based on this comparison, it may be desirable to calculate an update to the estimated image. The calculated update is then used to generate an updated reconstructed image. This updated reconstructed image is in turn used to generate an updated estimated sinogram that is a better match to the measured sinogram during subsequent iterations of the iterative process.

Accordingly, the method 1100 starts at step 1106 where an estimated sinogram 1102 is compared with a measured sinogram 1104. Statistically-weighted differences 1112 between the estimated sinogram 1102 and the measured sinogram 1104 are calculated, as indicated by step 1108. More particularly, the statistically weighted differences 1112 are determined based on statistical weighting factors 1110. As previously noted, a statistical model having the one or more statistical weighting factors 1110 is used to calculate the statistically-weighted differences 1112.

Subsequently, at least one image update 1116 to the estimated image is calculated based on the statistically-weighted differences 1112, as indicted by step 1114. This update step is typically performed as an optimization of an objective function. For example, the objective function may include a weighted least squares cost function or a log-likelihood function. It may be noted that during the iterative SIR process, the more closely the estimated sinogram matches the measured sinogram, the objective function is closer to its optimum.

Figure 12:
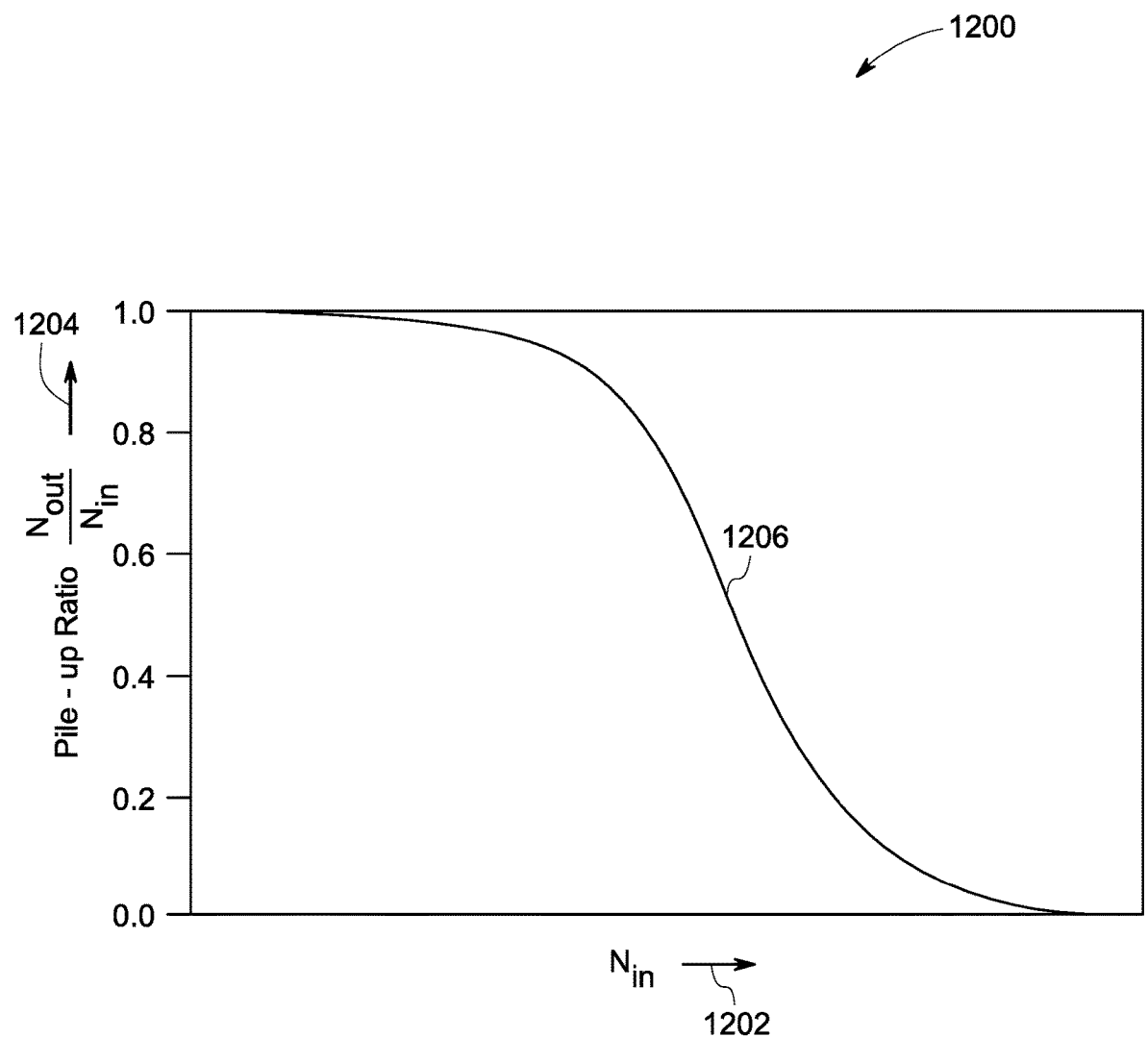
FIG. 12 depicts a graphical representation of a pile-up ratio, in accordance with aspects of the present specification.

Turning now to FIG. 12, a graphical representation 1200 of a pile-up ratio is depicted. Reference numeral 1202 represents the X-axis, while the Y-axis is represented by reference numeral 1204. Further, reference numeral 1206 generally graphically represents the dependence of the pile-up ratio on an input count rate. The pile-up ratio is a ratio of output counts or count rate divided by input counts or count rate. Also, the pile-up ratio is a useful value by which to compactly parameterize a pile-up noise correction.

In one embodiment, the pile-up ratio is calculated or measured as the number of output counts divided by the number of input counts. At low flux, the output counts are equal to the input counts, and hence the pile-up ratio equals one. As the count rate increases and pile-up occurs, some counts are lost and the pile-up ratio falls. At extremely high count rates, the output saturates or falls to zero, hence the pile-up ratio goes to zero. It may be noted that the pile-up ratio may be used to generate weights, which in turn may be used to generate updates to the estimated image in the processes characterized in FIG. 4 and FIG. 5.

FIG. 13 is a graphical representation 1300 of a noise pile-up correction factor as a function of a pile-up ratio. The X-axis is represented by reference numeral 1302 and indicates the pile-up ratio, while the Y-axis is represented by reference numeral 1304 and indicates the amplitude of a correction factor such as a noise correction factor. Further, reference numeral 1306 generally represents a pile-up correction factor. Also, reference numeral 1308 represents a linear extrapolation of the pile-up correction factor, to illustrate the linear behavior of the correction factor as the pile-up ratio approaches zero. In a certain embodiment, the projection data from each pixel is multiplied by a pile-up correction factor whose value is exemplified in the graphical representation 1300, based on the pile-up ratio in that pixel.

As illustrated in FIG. 13, the pile-up correction factor is equal to one for a zero pile-up ratio. Multiplying the measured counts or noise by 1 gives the original value. Hence, the correction for a low pile-up ratio leaves the counts or noise unchanged. The correction then falls with an approximately linear behavior. At a very high pile-up ratio, the correction factor approaches zero, thereby indicating that the corrected value approaches zero. Between these extremes, the correction factor varies smoothly with a more or less polynomial-like behavior.

In accordance with further aspects of the present specification, the methods of FIGS. 4-11 that are described in the context of iterative image reconstruction may also be applied to the context of basis material decomposition. In the example of basis material decomposition, it is desirable to estimate a number of basis material sinograms (or alternatively monochromatic sinograms) from a number of energy bin measurements or sinograms. The energy bin measurements may either be pre-corrected for pile-up or pile-up may be incorporated in the material decomposition (MD) models. Using an estimated set of basis material sinograms, a forward MD model is configured to compute an estimated set of energy bin sinograms. These estimated energy bin sinograms are compared to the measured energy bin sinograms. An objective function such as a weighted least squares cost function is used to define an iterative update step.

Embodiments of the present specification, thus, provide systems and methods for imaging that enhance the image quality of iterative reconstruction and/or material decomposition for PCCT imaging systems by applying the correct statistical models in forward projection and/or statistical weighting. In particular, in the systems and methods for imaging described hereinabove, the unique statistical properties of X-ray pile-up are incorporated into the noise model of an iterative algorithm for statistical image reconstruction or material decomposition for PCCT imaging systems.

Moreover, the systems and methods are configured to selectively down-weight the projection rays that suffer from the pile-up effect to reduce image artifacts in the final reconstructed images generated by the PCCT imaging systems, while the projection rays that are free of pile-up are comparatively boosted. Furthermore, the statistical weighting factors may be adaptively adjusted for pile-up correction, thereby furthering the reduction of the image artifacts in images generated by the PCCT imaging systems. The systems and methods are configured to effectively correct the pile-up corrupted signals in PCCT imaging systems. The methods disclosed may be applied to PCCT systems that provide projection data corresponding to one or more of total detected counts, counts in one or more energy bins, weighted sums of detected counts in one or more energy bins, and processed counts such as those that occur when material decomposition methods and/or mono-energetic processing methods are applied. Improved image quality provided by the present systems and methods will enable increased use of PCCT imaging systems.

It may be noted that the foregoing examples, demonstrations, and process steps that may be performed by certain components of the present systems, for example by the processing subsystem 112 and the noise correction platform 114 in particular, may be implemented by suitable code on a processor-based system. The processor-based system, for example, may include a general-purpose or a special-purpose computer. It may also be noted that different implementations of the present specification may perform some or all of the steps described herein in different orders or substantially concurrently.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of embodiments of the present specification may be shown in and/or described with respect to some drawings and not in others, this is for convenience only. It is to be understood that the described features, structures, and/or characteristics, illustrated in the figures and described herein, may be combined and/or used interchangeably in any suitable manner in the various embodiments, for example, to construct additional assemblies and methods for use in diagnostic imaging.

While only certain features of the present specification have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for imaging an object to be reconstructed, the method comprising:
   acquiring, via an imaging system, projection data corresponding to the object to be reconstructed;
   generating a measured sinogram based on the acquired projection data;
   formulating a forward model, wherein the forward model is representative of a characteristic of the imaging system;
   generating an estimated sinogram based on an estimated image of the object and the forward model;
   formulating a statistical model based on at least one of pile-up characteristics and dead time characteristics of a detector of the imaging system;
   determining an update corresponding to the estimated image based on the statistical model, the measured sinogram, and the estimated sinogram;
   updating the estimated image based on the determined update to generate an updated image of the object; and
   outputting a final image of the object.

2. The method of claim 1, further comprising acquiring at least one of the pile-up characteristics and dead time characteristics of the detector of the imaging system and system characteristics of the imaging system.

3. The method of claim 2, wherein formulating the forward model comprises modeling a behavior of the imaging system based on the system characteristics to generate the forward model.

4. The method of claim 1, wherein formulating the forward model comprises modeling a behavior of the imaging system based on the pile-up characteristics, the dead time characteristics, or a combination thereof.

5. The method of claim 1, wherein the statistical model is based on pulse responses of the detector, and wherein the statistical model comprises correction for pile-up in the mean and variance of measured counts of the detector.

6. The method of claim 5, further comprising estimating at least one parameter of the statistical model based on one or more of detector measurements corresponding to two or more neighboring detector channels and detector measurements corresponding to two or more energy bins.

7. The method of claim 5, further comprising iteratively estimating at least one parameter of the statistical model.

8. The method of claim 5, further comprising estimating at least one parameter of the statistical model based on at least one of a denoising technique, a variance reduction technique, a deep neural network, or combinations thereof.

9. The method of claim 1, wherein formulating the statistical model comprises:
   modeling a behavior of the detector of the imaging system based on at least one of the pile-up characteristics, the dead time characteristics, a measured detector behavior, or combinations thereof, to generate a detector behavior model;
   determining one or more noise correction factors based on the detector behavior model; and
   determining one or more statistical weighting factors based at least on the one or more noise correction factors.

10. The method of claim 9, wherein the one or more noise correction factors have a value of unity for the lowest count rate, and wherein the one or more noise correction factors asymptotically approach a zero value for high count rates.

11. The method of claim 1, wherein formulating the statistical model comprises:
   determining a simulated noise model based on at least one of the pile-up characteristics and the dead time characteristics;
   simulating noise corresponding to one or more configurations of the imaging system using the simulated noise model;
   measuring noise corresponding to the one or more configurations of the imaging system using a conventional noise model;
   comparing the simulated noise with the measured noise to determine one or more noise correction factors; and
   determining one or more statistical weighting factors based at least on the one or more noise correction factors.

12. The method of claim 11, further comprising adaptively adjusting the one or more statistical weighting factors to compensate for pile-up of a measurement signal.

13. The method of claim 12, wherein adaptively adjusting the one or more statistical weighting factors comprises determining a scaling function based on a detected signal level of the measurement signal, and wherein the scaling function is configured to selectively modify the one or more statistical weighting factors based on the measurement signal.

14. The method of claim 1, wherein formulating the statistical model comprises deriving a parametric statistical model based on the physics of pile-up of a measurement signal.

15. The method of claim 1, wherein formulating the statistical model comprises:
   simulating or measuring a pile-up process of the detector based on at least one of the pile-up characteristics and the dead time characteristics;
   determining one or more pile-up correction metrics based on a detector signal, wherein the one or more pile-up correction metrics comprise one or more of a pile-up ratio, a signal corrected for the pile-up, a deficiency signal corresponding to the pile-up; and
   determining one or more statistical weighting factors based at least on the one or more pile-up correction metrics.

16. The method of claim 1, wherein determining the update to the estimated image comprises:
   determining a statistically weighted difference between the measured sinogram and the estimated sinogram based on the one or more statistical weighting factors; and
   computing the update to the estimated image based on the statistically-weighted difference between the measured sinogram and the estimated sinogram.

17. The method of claim 1, further comprising:
   correcting the measured sinogram based on a pile-up model to generate a pile-up-corrected sinogram;
   determining the update to the estimated image based on the statistical model and the pile-up-corrected sinogram; and
   updating the estimated image based on the determined update to generate an updated image.

18. The method of claim 1, wherein the measured sinogram is a basis material sinogram, an energy bin sinogram, or both.

19. A system, comprising:
   a noise correction platform configured to:
      generate a measured sinogram based on projection data corresponding to an object to be reconstructed;
      formulate a forward model, wherein the forward model is representative of one or more characteristics of an imaging system;
      generate an estimated sinogram based on an estimated image, the forward model, or both the estimated image and the forward model;
      formulate a statistical model based on at least one of the pile-up characteristics and dead time characteristics of a detector of the imaging system;
      determine an update corresponding to the estimated image based on the statistical model and the estimated sinogram;
      update the estimated image based on the determined update to generate an updated image of the object; and
      output a final image of the object.

20. An imaging system for imaging an object to be reconstructed, the system comprising:
   an acquisition subsystem configured to acquire projection data corresponding to the object;
   a processing subsystem in operative association with the acquisition subsystem and comprising a noise correction platform, wherein the noise correction platform is configured to:
      generate a measured sinogram based on the projection data corresponding to the object;
      formulate a forward model, wherein the forward model is representative of a characteristic of the imaging system;
      generate an estimated sinogram based on an estimated image, the forward model, or both the estimated image and the forward model;
      formulate a statistical model based on at least one of pile-up characteristics and dead time characteristics of a detector of the imaging system;
      determine an update corresponding to the estimated image based on the statistical model and the estimated sinogram;
      update the estimated image based on the determined update to generate an updated image of the object;
      output a final image of the object; and
   a display configured to visualize at least one of the final image, the updated image, the measured sinogram, the estimated sinogram.

21. The imaging system of claim 20, wherein the imaging system is a photon counting computed tomography imaging system.

* * * * *